(12) United States Patent
Howe

(10) Patent No.: US 7,799,526 B2
(45) Date of Patent: Sep. 21, 2010

(54) PHOSPHOPROTEIN DETECTION REAGENT AND METHODS OF MAKING AND USING THE SAME

(75) Inventor: Alan Howe, Essex Junction, VT (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 10/719,990

(22) Filed: Nov. 21, 2003

(65) Prior Publication Data

US 2004/0146950 A1 Jul. 29, 2004

Related U.S. Application Data

(60) Provisional application No. 60/428,070, filed on Nov. 21, 2002.

(51) Int. Cl.
*C07D 239/88* (2006.01)
(52) U.S. Cl. ............... 435/6; 544/287; 548/110; 548/179; 548/304.1; 548/402; 548/405
(58) Field of Classification Search ............ 435/6
See application file for complete search history.

(56) References Cited

U.S. PATENT DOCUMENTS

| | | | | |
|---|---|---|---|---|
| 6,670,159 B1 * | 12/2003 | Savage et al. | ............... | 435/192 |
| 7,102,005 B2 * | 9/2006 | Agnew et al. | ............... | 544/287 |
| 7,183,392 B2 * | 2/2007 | Wagner et al. | ............ | 530/391.5 |
| 2002/0001857 A1 | 1/2002 | Vandermeeren et al. | | |
| 2002/0049307 A1 | 4/2002 | Aebersold et al. | | |
| 2002/0086009 A1 | 7/2002 | Ishiguro et al. | | |
| 2002/0086336 A1 | 7/2002 | Kramer et al. | | |
| 2008/0090255 A1 | 4/2008 | Howe | | |

FOREIGN PATENT DOCUMENTS

| | | |
|---|---|---|
| WO | WO 01/96869 | 12/2001 |
| WO | WO 02/04949 | 1/2002 |
| WO | WO 02/48390 | 6/2002 |

OTHER PUBLICATIONS

ChemGlobe (www.chemglobe.tsx.org, 2000).*
McHahan et al. (Analytical Biochemistry 1996; 236: 101-106).*
Molecular Probes (MP 21879, Pro-QTM Oligohistidine Blot Stain Kit #2, Sep. 27, 2001).*
Ehteshami et al. (J. Molecular Recognition 1996; 9: 733-737).*
Neville et al. (Protein Science 1997; 6: 2436-2445).*
Nieba et al. (Analytical Biochemistry 1997; 252: 217-228).*
Etheshami (1996 "Synthesis and Characterization of Bioaffinity Interactive Heterobifunctional Polyethylene Glycols", Ph.D. dissertation, University of Arizona).*
Zachariou et al. (Journal of Protein Chemistry 1995; 14: 419-430).*
Chaga et al. (J. Biochem. Biophys. Methods 2001; 49: 313-334, published on-line Oct. 2001).*
Zachariou et al. (Journal of Chromatography A 2000: 890; 95-116).*
Posewitz (Anal. Chem. 1999, 71: 2883-2892).*
Kaufmann et al., Use of antibodies for detection of phosphorylated proteins separated by two-dimensional gel electrophoresis, *Proteomics* 1:194-199 (2001).
Steen et al., Detection of Tyrosine Phosphorylated Peptides by Precursor Ion Scanning Quadrupole TOF Mass Spectrometry in Positive Ion Mode, *Analytical Chemistry* 73:1440-1448 (2001).
Wind et al., Analysis of Protein Phosphorylation by Capillary Liquid Chromatography Coupled to Element Mass Spectrometry with $^{31}$P Detection and to Electrospray Mass Spectrometry, *Analytical Chemistry* 73:29-35 (2001).
Reynolds et al., Detection and Phosphorylation of CREB (cAMP Response Element Binding Protein) Using Phospho-CREB (Ser 133) Antibody, *FASEB Journal* 16:A166 (2002).
Zhou et al., Detection and Sequencing of Phosphopeptides Affinity Bound to Immobilized Metal Ion Beads by Matrix-Assisted Laser Desorption/Ionization Mass Spectrometry, *Journal of the American Society for Mass Spectrometry* 11:273-282(2000).
Patton, Detection Technologies in Proteome Analysis, *Journal of Chromatography B* 771: 3-31 (2002).
Della Loggia et al., Methodological improvement of the protein phosphatase inhibition assay for the detection of okadaic acid in mussels, *Natural Toxins* 7:387-91 (1999).
Carmichael & AN, Using an enzyme linked immunosorbent assay (ELISA) and a protein phosphatase inhibition assay (PPIA) for the detection of microcystins and nodularins, *Natural Toxins* 7:377-85 (1999).
Ferrer et al., *A PDZ Domain-Based Detection System for Enzymatic Assays*, Analytical Biochemistry 301:207-216 (2002).
Berryman & Bretscher, Immunoblot Detection of Antigens in Immunoprecipitates, *BioTechniques* 31:744-746 (2001).
Bennett et al., Phosphopeptide detection and sequencing by matrix-assisted laser desorption/ionization quadrupole time-of-flight tandem mass spectrometry, *Journal of Mass Spectrometry* 37:179-190 (2002).
Becker et al., A sensitive fuorescence monitor for the detection of activated Ras: total chemical synthesis of site-specifcally labeled Ras binding domain of c-Raft immobilized on a surface, *Chemistry & Biology* 8:243-252 (2001).
Metcalf et al, Colorimetric Immuno-Protein Phosphatase Inhibition Assay for Specific Detection of Microcystins and Nodularins of Cyanobacteria, *Applied and Environmental Microbiology* 67:904-909 (2001).
Burnham et al., Detection of Phosphoryl-Dependent Interactions by Far-Western Gel Overlay, *Methods in Molecular Biology* 124:209-220 (2001).

(Continued)

*Primary Examiner*—Brandon J Fetterolf
(74) *Attorney, Agent, or Firm*—Jenkins, Wilson, Taylor & Hunt, P.A.

(57) ABSTRACT

A phosphoprotein detection reagent that selectively binds phosphoamino acids. Methods of generating and employing the reagent are also provided, as are methods of detecting modulation of protein phosphorylation are disclosed. Methods of detecting a change in state of a cell are also disclosed. Additionally, a kit for the detection of phosphoproteins is also disclosed.

25 Claims, 8 Drawing Sheets

OTHER PUBLICATIONS

Yanagida et al., Matrix assisted laser desorption/ionization-time of flight-mass spectrometry analysis of proteins detected by anti-phosphotyrosine antibody on two-dimensional-gels of fibrolast cell lysates after tumor necrosis factor-α stimulation, *Electrophoresis* 21:1890-1898 (2000).

Official Action corresponding to U.S. Appl. No. 11/901,875 dated Sep. 5, 2008.

Official Action corresponding to U.S. Appl. No. 11/901,875 dated Feb. 12, 2009.

* cited by examiner

PHOSPHOPROTEIN DETECTION REAGENT AND METHODS OF MAKING AND USING THE SAME

CROSS REFERENCE TO RELATED APPLICATIONS

This application is based on and claims priority to U.S. Provisional Application Ser. No. 60/428,070, filed Nov. 21, 2002, herein incorporated by reference in its entirety.

GRANT STATEMENT

This work is supported by grant CA92237 from the U.S. National Institutes of Health (NIH). Thus, the U.S. government has certain rights in the presently claimed subject matter.

TECHNICAL FIELD

The presently claimed subject matter generally relates to methods for detecting phosphorylated proteins. More particularly, the methods involve separating the proteins present in a cell lysate by electrophoresis, transferring the separated proteins to a solid support, and detecting the presence of phosphoproteins on the solid support using a phosphoprotein detection reagent.

Table of Abbreviations

| | |
|---|---|
| 2-DE | two-dimensional gel electrophoresis |
| $^{32}P$ | phosphorus-32 |
| $^{33}P$ | phosphorus-33 |
| Å | angstrom |
| AB-NTA | aminobutyl-nitriloacetic acid |
| AIDA | 2-(aminooxyethyl)iminodiacetic acid |
| $Al^{3+}$ | aluminum(III) ion |
| AP | alkaline phosphatase |
| CMPP | chelator-metal ion-phosphoprotein |
| EDC | N-ethyl-N'-(3-(dimethyl-aminopropyl) carbodiimide HCl |
| $Fe^{3+}$ | iron(III) ion |
| FPLC | fast performance liquid chromatography |
| $Ga^{3+}$ | gallium(III) ion |
| GST | glutathione-S-transferase |
| HRP | horseradish peroxidase |
| IDA | iminodiacetic acid |
| IMAC | immobilized metal ion affinity chromatography |
| kDa | kilodalton |
| $Lu^{3+}$ | lutetium(III) ion |
| M | Molar |
| mol | mole |
| MS | mass spectroscopy |
| Nck | adaptor protein that is a substrate for PKA |
| NHS | N-hydroxysuccinimdyl |
| $Ni^{2+}$ | nickel(II) ion |
| NTA | nitrilotriacetic acid |
| p-Ser | phosphorylated serine |
| P-tect | phosphoprotein detection reagent |
| p-Thr | phosphorylated threonine |
| p-Tyr | phosphorylated tyrosine |
| PAAAs | phosphoamino acid antibodies |
| PFP | penta-fluorophenyl |
| PKA | protein kinase A |
| PKAc | PKA catalytic subunit |
| PPDR | phosphoprotein detection reagent |
| Ponc-S | Ponceau-S |
| PSSAs | phospho-sequence-specific antibodies |
| PVDF | polyvinylidene fluoride |
| sA-HRP | streptavidin-conjugated horseradish peroxidase |
| $Sc^{3+}$ | scandium(III) ion |

-continued

| | |
|---|---|
| SDS-PAGE | sodium dodecyl sulfate polyacrylamide gel electrophoresis |
| SoMAC | soluble metal affinity complex |
| $Th^{3+}$ | thorium(III) ion |
| VASP | vasodilator-stimulated phosphoprotein |

Amino Acid Abbreviations

| Amino Acid | 3-Letter Code | 1-Letter Code |
|---|---|---|
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Proline | Pro | P |
| Phenylalanine | Phe | F |
| Serine | Ser | S |
| Threonine | Thr | T |
| Tryptophan | Trp | W |
| Tyrosine | Tyr | Y |
| Valine | Val | V |

BACKGROUND ART

With advances in mass spectrometric technologies and bioinformatics, it is possible to identify the majority of proteins from a cell extract after separation by two-dimensional electrophoresis (2-DE). However, amassing a catalog of proteins within a cell (the proteome) is of limited practical use without some knowledge of the functional state of those proteins. Reversible protein phosphorylation is the most abundant post-translational modification in eukaryotes and as such plays a crucial role in regulating protein function in both normal homeostatic processes as well as disease processes. Thus, identification and characterization of the phosphoproteins present within a cell under various conditions (the phosphoproteome) will generate a more useful molecular census of normal versus abnormal cellular states.

Given its crucial role in biology, the study of protein phosphorylation as it relates to normal and pathological physiology is one of the most important avenues of contemporary biomedical research. Specifically, identification of the major kinase and phosphatase substrates that are relevant to a given cellular process is of paramount importance if, at a biochemical level, complex biological events such as cell division, differentiation, and movement are to be defined.

Although simply stated, this task is truly formidable. It is currently thought that nearly one-third of all cellular proteins contain, at one time or another, covalently bound phosphate. See e.g., Hunter, 2000; Cohen, 2000. In addition, genomic studies suggest that the human genome encodes more than 1000 protein kinases and nearly 500 protein phosphatases to effect these modifications. See Cohen, 2000. As such, substantial interest and effort is currently being placed in phosphoproteomics: the identification and characterization of catalogs of phosphoproteins, and the changes in their phosphorylation status under various physiological conditions. See e.g., Ahn & Resing, 2001; Conrads et al., 2002; Mann et al., 2002. Of particular interest in phosphoproteomics is the identification of specific differences between the phosphoproteomes of normal and diseased cells in order to extrapolate these differences into exploitable targets for pharmacologic therapies.

The success of phosphoproteomics depends on the ability to detect and subsequently identify phosphorylated proteins in complex mixtures isolated from various experimental sources. This, in turn, will require reliable detection methods that are compatible with contemporary protein identification technologies such as peptide microsequencing and mass spectrometry. The panel of currently available detection methods, however, leaves an urgent need for novel, more powerful methods.

Current methods for detecting or selectively enriching for phosphorylated proteins can be divided into three categories—radioisotopic, immunological, and chromatographic. While each method has been used successfully under certain conditions, each suffers from its own significant limitations as well. See e.g., Kaufmann et al., 2001; Conrads et al., 2002.

Using radioisotopic methods, phosphoproteins are most commonly detected by autoradiography of individual proteins or protein mixtures isolated from cells cultured in the presence of phosphate containing $^{32}$P (or, less frequently, $^{33}$P) at its core. While the use of radioactive phosphate provides a fairly sensitive method to label a large number of proteins using a technically uncomplicated procedure, it has several significant drawbacks. Radioactive labeling requires "metabolic access" to the biological sample (e.g. cultured cells), precluding its application to tissues and clinical samples. Additionally, even when access is available, the labeling period itself poses problems. It must be long enough to allow free radioactive phosphate to equilibrate with the cellular ATP pool, but brief enough to prevent cellular damage or stress due to the radioisotope or the reduced concentration of total phosphate in typical labeling media. Also, differences in phosphate turnover among proteins and individual amino acids result in preferential labeling of proteins with rapid phosphate turnover rates as well as unequal incorporation of $^{32}$P into serine vs. threonine vs. tyrosine residues. Sefton, 1991. Furthermore, the use of radioactivity presents considerable hazardous material concerns and waste storage/disposal costs. The final, and arguably most significant, limitation of radioactive phosphate labeling is that the radioactive samples generated are almost universally rejected by commercial protein sequencing and mass spectrometry (MS) facilities. Thus, the precious sample(s) must be either enzymatically dephosphorylated (which can be technically difficult and prevents subsequent determination of the modified residue(s)) or kept shelved and unanalyzed for weeks or months until the level of radioactivity has decayed to background levels.

Some of the shortcomings of radioisotopic labeling can be addressed by using antibodies that specifically recognize the phosphorylated forms of certain amino acids. Principally, antibody-based methods do not require prior labeling or other manipulation of the biological source of phosphoproteins and they present no real safety or hazardous material concerns. The relevant antibodies fall into two classes. Phosphoamino acid antibodies (PAAAs) recognize the individual phosphorylated residue (i.e. p-Ser, p-Thr, or p-Tyr) regardless of the surrounding amino acid composition. Phospho-sequence specific antibodies (PSSAs) recognize the phosphorylated residue only within the context of a specific amino acid sequence. While PSSAs have proven useful in the analysis of single, specific phosphoproteins (e.g. mitogen-activated protein kinase, retinoblastoma protein), their specificity precludes their use in identifying unknown phosphoproteins in complex mixtures.

PAAAs are more useful in general phosphoproteomic analyses, but still suffer limitations. Antibodies against p-Tyr have proven most useful. See e.g., Cooper et al., 1983; Kaufmann et al, 2001. Generally, they are of sufficiently high affinity to allow detection of low-abundance proteins by immunoblotting and can also be used to enrich tyrosine-phosphorylated proteins by immunoprecipitation and immunoaffinity chromatography. Their ability to specifically recognize p-Tyr regardless of the surrounding sequence is less than optimal, however. See e.g., Cooper et al., 1983; Kaufmann et al., 2001; Conrads et al, 2002; Mann et al., 2002.

The major limitation for p-Tyr antibodies in phosphoproteomics is, again, their specificity. While tyrosine-phosphorylated proteins are an important fraction of total cellular phosphoproteins, there are also the least abundant by far. Indeed, the ratio of p-Ser, p-Thr, and p-Tyr in cells is estimated to be approximately 1800:200:1. Mann et al., 2002. Thus, use of p-Tyr antibodies can be expected to detect, at best, 0.05% of all phosphoproteins in a cell. Unfortunately, the use of anti-p-Ser and anti-p-Thr antibodies to detect the remaining 99.95% has not been very successful. Due to their relatively small size, these phosphoamino acids are substantially less antigenic than p-Tyr. Attempts to create anti-p-Ser and anti-p-Thr antibodies have resulted in antibody preparations that are alternatively 1) specific but low-affinity; 2) high-affinity but bind to p-Ser, p-Thr, and p-Tyr with comparable strength; or 3) high-affinity but bind only a restricted subset of protein sequences containing their target phosphoamino acid. See e.g., Kaufmann et al., 2001; Mann et al., 2002. Thus, none of these antibodies are particularly useful to generalized phosphoproteomic analysis.

Other major complications of using immunological reagents for phosphoprotein detection are encountered after the actual detection. Immunoblotting is best performed after blocking unoccupied sites on the solid-phase support with protein solutions, which interferes with subsequent microchemical techniques required for protein identification. Indeed, the antibodies themselves can complicate identification of the target phosphoprotein. On the other hand, removal of the antibody requires relatively harsh treatments (e.g. heat plus detergent and reducing agents), which can negatively impact subsequent attempts at protein sequencing and mass spectrometry of the detected proteins. See e.g., Kaufmann et al., 2001; Conrads et al., 2002. Thus, while immunological techniques offer certain advantages over metabolic labeling, difficulties remain in applying current anti-phosphoamino acid antibodies as phosphoproteomic reagents.

A third method involves chromatographic separation of phosphorylated from non-phosphorylated proteins. Chromatographic separation of phosphoproteins or phosphopeptides can reduce "proteomic noise" by eliminating non-phosphorylated proteins from analytical samples before MS. The use of phospho-immunoaffinity columns has been employed, but this strategy suffers from the limitations discussed above for other antibody-based methods.

Other techniques have been described that employ specific chemical derivatization of phosphate groups with heterologous functional groups that allow selective chromatographic separation of the once-phosphorylated species. Oda et al., 2001; Zhou et al., 2001. One such approach involves replacement of the phosphate groups of serine and threonine phosphopeptides by ethanedithiol via a β-elimination reaction, followed by tagging the derived peptides with a biotin affinity tag, which allows separation from non-phosphorylated peptides by avidin affinity chromatography. Oda et al., 2001. One drawback of this approach is the low reactivity of phosphothreonine and non-reactivity of phosphotyrosine residues in β-elimination reactions.

A second approach involves alkylation of existing cysteine residues followed by carbodiimide-catalyzed reaction of phosphates with cystamine to introduce a free sulfhydryl group, which allows derivatized peptides to be captured on iodoacetic beads. Zhou et al., 2001. While broadly reactive with all three major phosphoamino acids, the method involves a six-step derivatization/purification protocol that requires more than 13 hours to complete and produces only a 20% yield.

Thus, these techniques have their own significant and unique drawbacks. They also suffer from the same major limitation that all other chromatographic methods do, namely that a given method will (theoretically) retain any and all phosphoproteins in a given sample, even those for which the phosphorylation state does not change between relevant "before and after" conditions. This inability to cull experimentally relevant targets from the entire pool of cellular phosphoproteins introduces significant "noise" into the data, the elimination of which is a significant ongoing difficulty in the art. See e.g., Oda et al., 2001; Steen et al., 2001; Zhou et al., 2001; Ficarro et al., 2002; Mann et al., 2002.

Thus, there exists a long-felt and continuing need in the art for new methodologies that will allow rapid, safe, specific, and complete phosphoprotein detection that are compatible with mass spectrometric identification techniques. The presently claimed subject matter addresses this and other needs in the art.

SUMMARY

This Summary lists several embodiments of the presently claimed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

The presently claimed subject matter provides a phosphoprotein detection reagent that can be used for detecting phosphoproteins. The reagent of the presently claimed subject matter comprises a chelator-metal ion moiety and an detectable moiety conjugated to the chelator-metal ion moiety, wherein the chelator-metal ion moiety selectively binds to a phosphorylated amino acid residue in a phosphoprotein if present to create a chelator-metal ion-phosphoprotein (CMPP) complex, and the detectable moiety allows the CMPP complex to be detected if present. In one embodiment, the reagent is soluble in an aqueous medium. In one embodiment, the chelator is nitriloacetic acid. In another embodiment, the chelator is iminodiacetic acid. In one embodiment, the metal ion is chosen from the group consisting of $Fe^{3+}$, $Cu^{2+}$, $Al^{3+}$, $Yb^{3+}$, $Zn^{2+}$, $Ni^{2+}$, $Co^{2+}$, and $Ga^{3+}$. In another embodiment, the metal ion is $Fe^{3+}$. In still another embodiment, the metal ion is $Ga^{3+}$. In one embodiment, the detectable moiety is biotin. In one embodiment, the reagent of the presently claimed subject matter further comprises a spacer between the chelator-metal ion moiety and the detectable moiety.

The presently claimed subject matter also provides a method for synthesizing a phosphoprotein detection reagent that is soluble in an aqueous medium. In one embodiment, the method comprises (a) reacting a polydentate chelator donor molecule with an detectable moiety donor under conditions wherein a detectable moiety is transferred to a polydentate chelator to form a chelator-detectable moiety complex; and (b) mixing the chelator-detectable moiety complex and a metal ion-containing solution under conditions wherein the chelator-detectable moiety complex coordinates the metal ion, forming a phosphoprotein detection reagent that is soluble in aqueous medium. In one embodiment, the chelator donor molecule is selected from the group consisting of 2-(aminooxyethyl)iminodiacetic acid (AIDA), aminobutyl-nitriloacetic acid (AB-NTA), and iminodiacetic acid (IDA). In one embodiment, the detectable moiety donor molecule is selected from the group consisting of sulfo-N-hydroxysuccinimidyl-biotin (sulfo-NHS-biotin), sulfosuccinimidyl-6-(biotinamido)hexanoate (sulfo-NHS-LC-biotin), sulfosuccinimidyl-6-(biotinamido)-6-hexanimido hexanoate (sulfo-NHS-LC-LC-biotin), and penta-fluorophenyl-biotin. In one embodiment, the detectable moiety donor is present in the reacting step in a molar excess over the polydentate chelator donor molecule. In one embodiment, the chelator-detectable moiety complex and a metal ion-containing solution are present in equimolar concentrations in the mixing step.

The presently claimed subject matter also provides a method for detecting a phosphoprotein. In one embodiment, the method comprises (a) obtaining a protein-containing solution; (b) separating the proteins present in the solution from each other; (c) contacting the proteins with a reagent under conditions wherein the reagent will selectively bind to a phosphorylated amino acid residue present within the proteins to form a reagent/amino acid complex, the reagent comprising a chelator-metal ion moiety and an detectable moiety conjugated to the chelator-metal ion moiety, wherein the chelator-metal ion moiety selectively binds to a phosphorylated amino acid residue in a phosphoprotein if present to create a chelator-metal ion-phosphoprotein (CMPP) complex, and the detectable moiety allows the CMPP complex to be detected if present; and (d) detecting the reagent/amino acid complex, wherein the detection of the reagent/amino acid complex detects a phosphoprotein. In one embodiment, the separating is by electrophoresis. In another embodiment, the separating is by two-dimensional gel electrophoresis. In still another embodiment, the separating is by sodium dodecyl sulfate polyacrylamide gel electrophoresis. In one embodiment, the conditions wherein the reagent will selectively bind to a phosphorylated amino acid residue present within the immobilized proteins to form a reagent/amino acid complex comprise permissive conditions followed by washing the solid support to remove unbound reagent. In one embodiment, the permissive conditions comprise contacting the reagent and immobilized proteins at a pH between about 5.0 and 7.0, and washing at a pH between about 6.9 and 9.5. In one embodiment, the detecting is via a chemiluminescent assay. In another embodiment, the detecting is via fluorescence. In still another embodiment, the detecting is via a calorimetric assay. In one embodiment, the method further comprises the step of immobilizing the proteins on a solid support after the separating step and prior to the contacting step. In one embodiment, the immobilizing is by electrophoretic transfer. In one embodiment, the solid support is a PVDF membrane. In one embodiment, the method further comprises treating the proteins with a carboxy-blocking reagent after the separating step and prior to the contacting step. In one embodiment, the carboxy-blocking reagent is selected from the group consisting of methanolic HCl, a carbodiimide, and Woodward's Reagent "K".

The presently claimed subject matter also provides a method for detecting a change in phosphorylation status of a protein present within a target tissue in response to a change in state. In one embodiment, the method comprises (a) obtaining a protein lysate from a cell from the target tissue prior to the change in state; (b) separating the proteins present in the lysate from each other; (c) contacting the proteins with a reagent under conditions wherein the reagent will selectively bind to a phosphorylated amino acid residue present within the proteins to form a reagent/amino acid complex, the reagent comprising a chelator-metal ion moiety and an detectable moiety conjugated to the chelator-metal ion moiety, wherein the chelator-metal ion moiety selectively binds to a phosphorylated amino acid residue in a phosphoprotein if present to create a chelator-metal ion-phosphoprotein (CMPP) complex, and the detectable moiety allows the CMPP complex to be detected if present; (d) detecting the reagent/amino acid complex, wherein the reagent/amino acid complex is indicative of a phosphoprotein in the cell lysate; (e) creating a profile indicative of the detected phosphoproteins of the lysate; (f) obtaining a protein lysate from a cell from the target tissue after the change in state; (g) repeating steps b) through e) for the lysate from a cell from the target tissue after the change in state; and (h) comparing the profile from the lysate from the cell from the target tissue prior to the change in state to the profile from the lysate from the cell from the target tissue after the change in state, wherein a difference between the two profiles is indicative of a change in the phosphorylation status of a protein present within the target tissue in response to the change in state of the target tissue. In one embodiment, the change in state is from a non-neoplastic to a neoplastic state. In another embodiment, the change in state is from a non-differentiated to a differentiated state. In another embodiment, the change in state is from a benign state to a malignant state. In still another embodiment, the change in state is from an unstimulated to a stimulated state. In one embodiment, the method further comprises immobilizing the proteins present in the solution onto a solid support prior to the detecting step.

The presently claimed subject matter also provides a method for early diagnosis of a change in state of a target tissue. In one embodiment, the method comprises (a) detecting a phosphorylation state of a protein in a target tissue and (b) comparing the detected phosphorylation state of the protein to a standard profile, wherein the comparison identifies a change in state of the target tissue.

The presently claimed subject matter also provides a kit comprising a PPDR. In one embodiment, the kit further comprises instructions for using the PPDR. In another embodiment, the kit further comprises a secondary reagent for detecting the PPDR.

Accordingly, it is an object of the presently claimed subject matter to provide a method for detecting phosphoproteins among a mixture of proteins. This and other objects are achieved in whole or in part by the presently claimed subject matter.

An object of the presently claimed subject matter having been stated above, other objects and advantages of the presently claimed subject matter will become apparent to those of ordinary skill in the art after a study of the following description of the presently claimed subject matter, Drawings, and non-limiting Examples.

BRIEF DESCRIPTION OF THE DRAWINGS

In FIG. 1, phosphoproteins common between the two samples are depicted as black circles. Proteins for which the phosphorylation state has changed (depicted as hatched circles in the bottom panel) are picked for subsequent identification and analysis by mass spectrometry (MS) in step E.

FIG. 5A shows the reaction of acidic side chains with methyl acetate under acidic conditions (i.e. methanolic HCl) to form carboxymethyl esters.

FIG. 5B shows the reaction of N-ethyl-N'-3-(dimethylaminopropyl)carbodiimide HCl (EDC) with an acidic group to form a reactive intermediate that condenses with primary amines (methylamine is shown) to form an amide. Neither product binds to metal ion chelates, and therefore, not to SoMACs.

DETAILED DESCRIPTION

Figure 1:
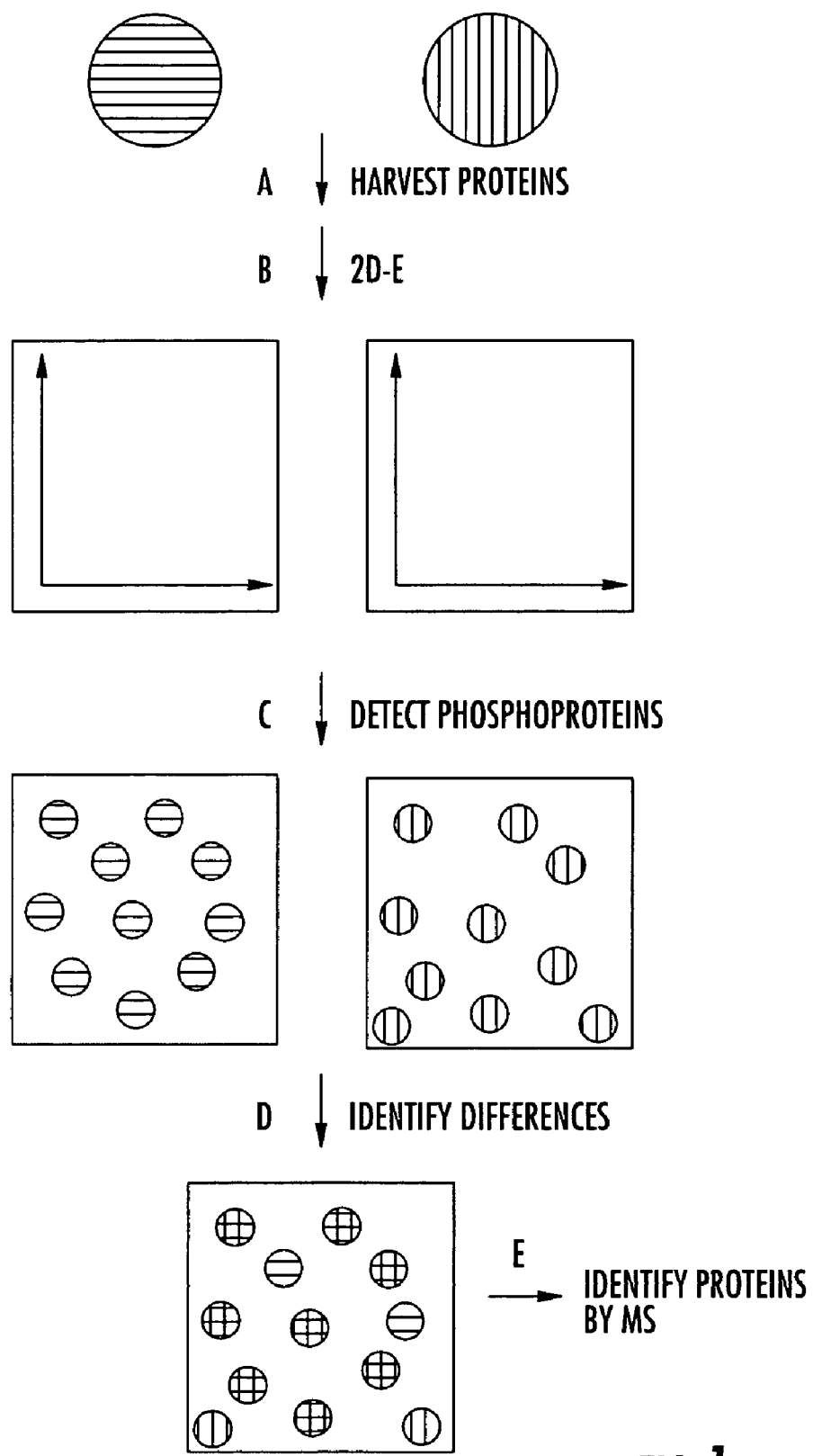
FIG. 1 depicts a simplified protocol for phosphoproteomics. Proteins from two experimental conditions, for example "before" (horizontal hatching) and "after" (vertical hatching) cells in culture, are harvested in step A and separated by two-dimensional gel electrophoresis in step B. The phosphorylated proteins present in the samples are detected in step C and proteins for which the phosphorylation state changes between the two conditions are identified in step D.

Although originally thought to apply only to the control of glycogen metabolism (Fischer, 1997), protein phosphorylation is now recognized to be an integral regulatory facet of nearly every cellular process. See, e.g. Fischer, 1997; Cohen, 2000; Hunter, 1995. Phosphorylation can affect nearly every aspect of protein function, including biochemical activity, stability, intermolecular interactions, and subcellular movement and/or location. See, e.g. Cohen, 2000; Johnson & Lewis, 2001. The physiological importance of phosphorylation is underscored by the fact that genetic and pharmacologic alterations in phosphorylation result in a variety of pathological states including cancer, neurological defects, acute toxicological illnesses, and diabetes. See e.g., Hunter, 1998; Blume-Jensen & Hunter, 2001; Ukkola & Santaniemi, 2002; Cohen, 2002b; Lau et al., 2002. Such genetic and pharmacologic alterations include, for example, activation of oncogenic kinases such as Abl (Sawyers, 2002) and Raf (Lee & McCubrey, 2002) and exposure to kinase- or phosphatase-specific toxins such as phorbol esters and microcystins (Cohen, 2002).

Given the role reversible phosphorylation plays in both normal and abnormal cellular processes, it would be extremely valuable to create a catalog of proteins within a cell for which the phosphorylation states change as a result of the cell's progression from one condition to another. In order to assemble these catalogs, new reagents and methods will have to be produced for detecting proteins undergoing such phosphorylation state changes. Thus, the presently claimed subject matter generally relates to reagents and methods for detecting a phosphoprotein. In one embodiment, the presence of a phosphoprotein in a cell lysate is detected after electrophoretic separation and transfer of the proteins in a cell lysate to a solid support.

I. Phosphoprotein Detection Reagent (PPDR)
    I.A. Introduction

One general method useful for the protein purification is immobilized metal ion affinity chromatography (IMAC). Gaberc-Porekar & Menart, 2001. See also Porath et al., 1975. IMAC employs a metal ion partially coordinated by a polydentate chelating group coupled to a solid-phase material. The remaining coordination sites on the metal ion provide affinity for certain amino acids or other moieties present in proteins and peptides. The most common manifestation of IMAC in use today is Ni-based IMAC for purification of proteins containing poly-His tagging sequences. See Hochuli et al., 1987; Hochuli, 1988. See also U.S. Pat. No. 4,423,158 to Porath and U.S. Pat. Nos. 4,877,830 and 5,047,513 to Dobeli et al. Poly-His tagging sequences are not present in native proteins. Thus, poly-His tagging sequence are usually added in vitro to the proteins to be purified in this approach to Ni-based IMAC.

It is possible to alter the specificity of metal ion binding in IMAC by varying the chelated metal ion or other parameters. Porath & Olin, 1983; Ramadan & Porath, 1985; Andersson & Porath, 1986; Muszynska et al., 1986. One such variation involves the use of hard Lewis acid ions (initially $Fe^{3+}$, followed by $Al^{3+}$ and $Ga^{3+}$) to form resins with higher affinity and specificity for phosphate-containing proteins and peptides. Andersson & Porath, 1986; Muszynska et al., 1986; Muszynska et al., 1992; Li & Dass, 1999; Posewitz & Tempst, 1999; Xhou et al., 2000. The use of such resins is currently limited to separating phosphorylated and non-phosphorylated peptides from a single, digested protein, not from complex protein mixtures. See Li & Dass, 1999; Posewitz & Tempst, 1999; Stensballe et al., 2001; Ficarro et al., 2002; Raska et al., 2002. Additionally, the physical form of the IMAC resin, namely its immobilization on a solid phase material, precludes its usefulness in solution to detect the presence of phosphoproteins that have been electrophoretically separated and transferred to a solid support.

I.B. Phosphate-Specific Detection Reagent

Figure 2:
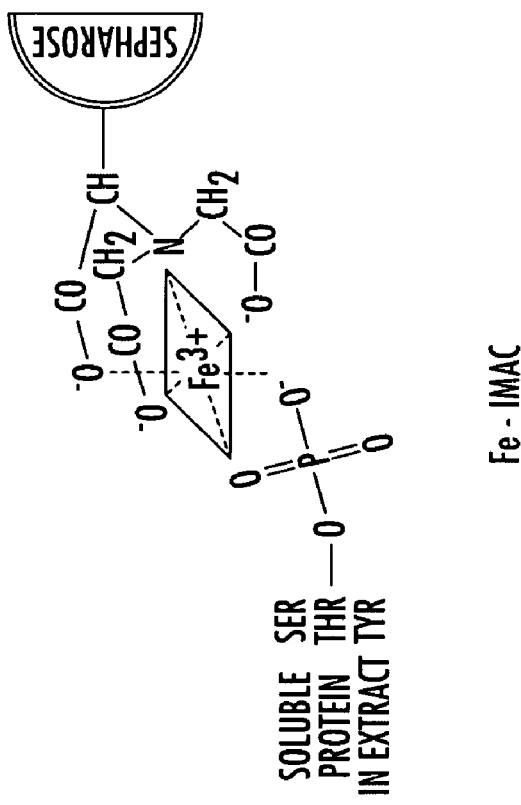
FIG. 2 depicts the evolution of the phosphoprotein detection reagent from immobilized metal affinity chromatography (IMAC). The original incarnation of IMAC involves a chelated $Ni^{2+}$ ion, which, when conjugated to a solid support, is used as an affinity matrix for poly-His-tagged proteins. Substitution of $Fe^{3+}$ for $Ni^{2+}$ changes the specificity from His to the more highly polar and charged phosphate moiety. Conjugation of the chelate to biotin rather than to a solid matrix produces a soluble agent with high fidelity phosphate binding that can be used to probe for phosphoproteins immobilized on a membrane.
Figure 2:
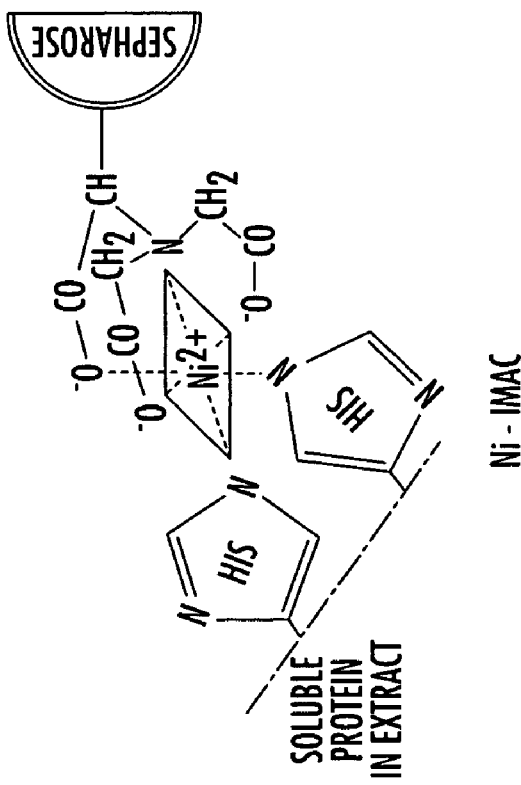
Figure 2:
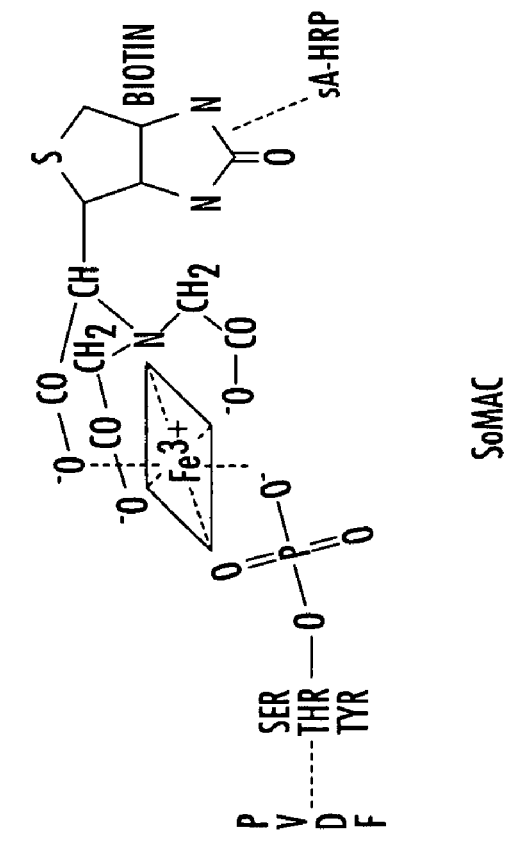

Whether a soluble form of the chelator-metal ion complex might be used as a reagent to detect phosphoproteins was evaluated. In one embodiment, the phosphoproteins were electrophoretically separated and transferred to a nitrocellulose or PVDF membrane. A putative soluble metal-ion affinity complex (SoMAC) would include a polydentate chelating moiety similar to those that have proven useful as solid-phase materials, but coupled to a small functional group that allows strong, specific interaction with commercially available secondary reagents. See FIG. 2.

In one embodiment, a PPDR of the presently claimed subject matter comprises a SoMAC, i.e. a chemical that is soluble in aqueous solution and that comprises a chelator-metal ion moiety conjugated to a detectable moiety, wherein the chelator-metal ion moiety can selectively bind to a phosphorylated amino acid residue of a phosphoprotein. The binding of the chelator-metal ion moiety to a phosphoamino acid creates a chelator-metal ion-phosphoprotein (CMPP) complex, which is detected via the detectable moiety.

As used herein, the term "soluble" refers to a reagent that can be dissolved in an aqueous solution. A soluble PPDR can be added in an aqueous solution to a cell lysate comprising a phosphoprotein, in contrast to an immobilized reagent such as an IMAC column. Thus, in one embodiment, the PPDR of the presently claimed subject matter is soluble in aqueous medium.

As used herein, the term "phosphoprotein" refers to a protein that has been post-translationally modified such that a phosphate group has been transferred to an amino acid residue of the protein. The phosphate group can be transferred by enzymatic action within a cell to any amino acid, including, but not limited to serine, threonine, and tyrosine.

As used herein, the term "chelator-metal ion moiety" refers to a polydentate chelator molecule to which a metal ion is coordinated. A polydentate chelator molecule includes, but is not limited to bidentate, tridentate, tetradentate, and pentadentate chelators. As such, representative chelators include, but are not limited to aminohydroxamic acid, salicylaldehyde, 8-hydroxy-quinoline, iminodiacetic acid (IDA), dipicolylamine, ortho-phosphoserine, N-(2-pyridylmethyl)aminoacetate, 2,6-diaminomethylpyridine, nitrilotriacetic acid (NTA), carboxymethylated aspartic acid, and N,N,N'-tris(carboxymethyl)ethylenediamine. In one embodiment of the presently claimed subject matter, the polydentate chelator is IDA. In another embodiment, the polydentate chelator is NTA.

Various metal ions can be coordinated to the chelator to form a chelator-metal ion moiety. Metal ions for use in the presently claimed subject matter include, but are not limited to $Fe^{3+}$, $Cu^{2+}$, $Al^{3+}$, $Yb^{3+}$, $Zn^{2+}$, $Ni^{2+}$, $Co^{2+}$, and $Ga^{3+}$. In one embodiment of the presently claimed subject matter, the metal ion is $Ga^{3+}$. In another embodiment, the metal ion is $Fe^{3+}$. In one embodiment, the presently claimed subject matter comprises a chelator-metal ion moiety that comprises $Fe^{3+}$-coordinated NTA.

As used herein, the term "detectable moiety" refers to a molecule or a complex of molecules that can be conjugated to a polydentate chelator and allows the PPDR to be detected, either directly or by employing secondary reagents (defined below). In one embodiment, the detectable moiety is biotin.

As used herein, the terms "detecting", "detected", and "detection" refer to confirming the presence of a detectable moiety by observing the occurrence of a detectable signal, such as a radiologic, colorimetric, fluoroscopic, chemiluminescent, or spectroscopic signal that will appear exclusively in the presence of the detectable moiety.

The terms "indicator" and "secondary reagent" are used interchangeably and refer to a chemical species or compound that is readily detectable using a standard detection technique, such as dark versus light detection, fluorescence or chemiluminescence spectrophotometry, scintillation spectroscopy, chromatography, liquid chromatography/mass spectroscopy (LC/MS), colorimetry, and the like. Representative indicators thus include, but are not limited to fluorogenic or fluorescent compounds, chemiluminescent compounds, colorimetric compounds, UV/VIS absorbing compounds, radionucleotides, and combinations thereof. In one embodiment, the indicator is a fluorescent molecule.

Appropriate indicators and secondary reagents for use with the presently claimed subject matter depend on the particular embodiment of the PPDR being used. For example, if the detectable moiety is biotin, appropriate secondary reagents include, but are not limited to streptavidin, avidin, and anti-biotin antibodies, which are commercially available. These secondary reagents are typically conjugated to an enzyme for which a convenient assay system is available or to another detectible marker. In accordance with the presently claimed subject matter, the enzyme can be a peroxidase, for example horseradish peroxidase (HRP), or a β-galactosidase. Enzyme-conjugated indicators and secondary reagents are available from several manufacturers, including Pierce Biotechnology, Inc. (Rockford, Ill., United States of America). Alternatively, the secondary reagent can comprise a fluorescent molecule.

In one embodiment, the detectable moiety comprises a biotin molecule, which is detected using HRP-conjugated streptavidin. Biotin is known to bind with high affinity to streptavidin. There are several commercially available assays for HRP, including chemiluminescent assays (e.g. the ECL Kits available from Amersham Biosciences Corporation of Piscataway, N.J., United States of America). In one embodiment, a PPDR containing a biotin moiety is bound to a phosphoprotein. The phosphoprotein is then detected by detecting the presence of the biotin molecule in the bound PPDR. This is accomplished by binding an HRP-conjugated streptavidin molecule to the biotin molecule, and detecting the presence of the HRP enzyme using a chemiluminescent HRP substrate.

As used herein, the term "selectively binds" refers to a binding reaction that is determinative of the presence of the phosphoprotein in a heterogeneous population of proteins and other biological materials. Thus, under designated conditions, the specified PPDR binds to a phosphoprotein and does not show significant binding to non-phosphorylated proteins present in the lysate or on the solid support. Conditions that can facilitate selective binding of the reagent to a phosphoprotein can include but are not limited to high salt and mildly acidic pH.

As used herein, the term "spacer" refers to a molecule placed between the detectable moiety and the chelator moiety for the purpose of separating the two spatially. Thus, in one embodiment the presently claimed subject matter comprises a PPDR having the general formula chelator-metal ion moiety—spacer—detectable moiety, where the chelator-metal ion moiety and the detectable moiety are bridged by a spacer unit comprising an organic unit, an inorganic unit, a biological unit, and combinations thereof. Examples of representative spacer units include, but are not limited to, a charged functional group or domain; a hydrophobic domain; a hydrophilic domain; a functional group or domain having a moiety selected from a group including, but not limited to, —S, —N, —N=N—, halogen (—I, —Br, —F, —Cl), —OR, —R—O—R, —HOOCR, —HOR (where R=hydrogen, alkyl, alkenyl, alkynyl, or aryl as defined herein below, and R may be the same moiety or different moieties); and functional groups with variable ratios of charged, hydrophobic, and/or hydrophilic domains. Other examples of representative spacer units include $RHN(CH_2)_2NHR$, RNHR, and RNH-CONHR, where R=hydrogen, alkyl, alkenyl, alkynyl, or aryl as defined herein below, and R may be the same moiety or different moieties.

Within the definition of R generally, the term "alkyl" is meant to have its art-recognized meaning. Substituted and unsubstituted, as well as branched and unbranched $C_1$ through $C_{20}$-alkyls are particularly contemplated, including methyl-, ethyl-, propyl-, isopropyl-, n-propyl- and butyl-. Exemplary substituents include —OH and —OR', wherein R' is a $C_{1-4}$ alkyl.

Within the definition of R generally, the term "alkenyl" is meant to have its art-recognized meaning. Substituted and unsubstituted, as well as branched and unbranched $C_1$ through $C_{20}$-alkenyls having at least one double bond at varying locations are particularly contemplated, including vinyl-, allyl- and isopropenyl-. Exemplary substituents include —OH and —OR', wherein R' is a $C_{1-4}$ alkyl.

Within the definition of R generally, the term "alkynyl" is meant to have its art-recognized meaning. Substituted and unsubstituted, as well as branched and unbranched $C_1$ through $C_{20}$-alkynyls having at least one triple bond at varying locations are particularly contemplated, including ethynyl-, propynyl-, and butynyl-. Exemplary substituents include —OH and —OR', wherein R' is a $C_{1-4}$ alkyl.

Within the definition of R generally, the term "aryl" is meant to have its art-recognized meaning. Substituted, unsubstituted, and multiple ring aryl groups are particularly contemplated, including benzyl-, ethylbenzyl-, phenyl-, xylene substituents, toluene substituents, styrene substituents, and naphthalene substituents.

More particularly, the spacer unit can be chosen from the following group: $O-CO-(CH_2)_4$; $O-CO-(CH_2)_5-$ NH—CO—(CH$_2$)$_4$; C—CO—(CH$_2$)$_2$—(SH$_2$)$_2$—(CH$_2$)$_2$—NH—CO—(CH$_2$)$_3$; and O—CO—(CH$_2$)$_5$—NH—CO—(CH$_2$)$_4$. Biotinylation reagents incorporating these spacers of between 13 and 30 angstroms are commercially available from Pierce Biotechnology, Inc. (Rockford, Ill., United States of America).

I.C. Synthesis of a PPDR

The synthesis of a PPDR of the presently claimed subject matter involves the production of a chelator-detectable moiety, to which a metal ion is subsequently coordinated. The indicator used to detect the chelator-detectable moiety can be any molecule that can be used to detect the detectable moiety either directly or indirectly, including, but not limited to a fluorescent molecule, an enzyme such as a peroxidase or beta-galactosidase, and biotin. In one embodiment of the presently claimed subject matter, the detectable moiety is biotin and the indicator is HRP-conjugated streptavidin.

The chelator component of the chelator-detectable moiety comprises a polydentate chelator. In one embodiment, a polydentate chelator is NTA. In one embodiment, the chelator-detectable moiety is biotin-conjugated NTA. A form of biotin-conjugated NTA is commercially available (biotin-X-NTA, cat# B-11790, Molecular Probes, Inc., Eugene, Oreg., United States of America).

Figure 6:
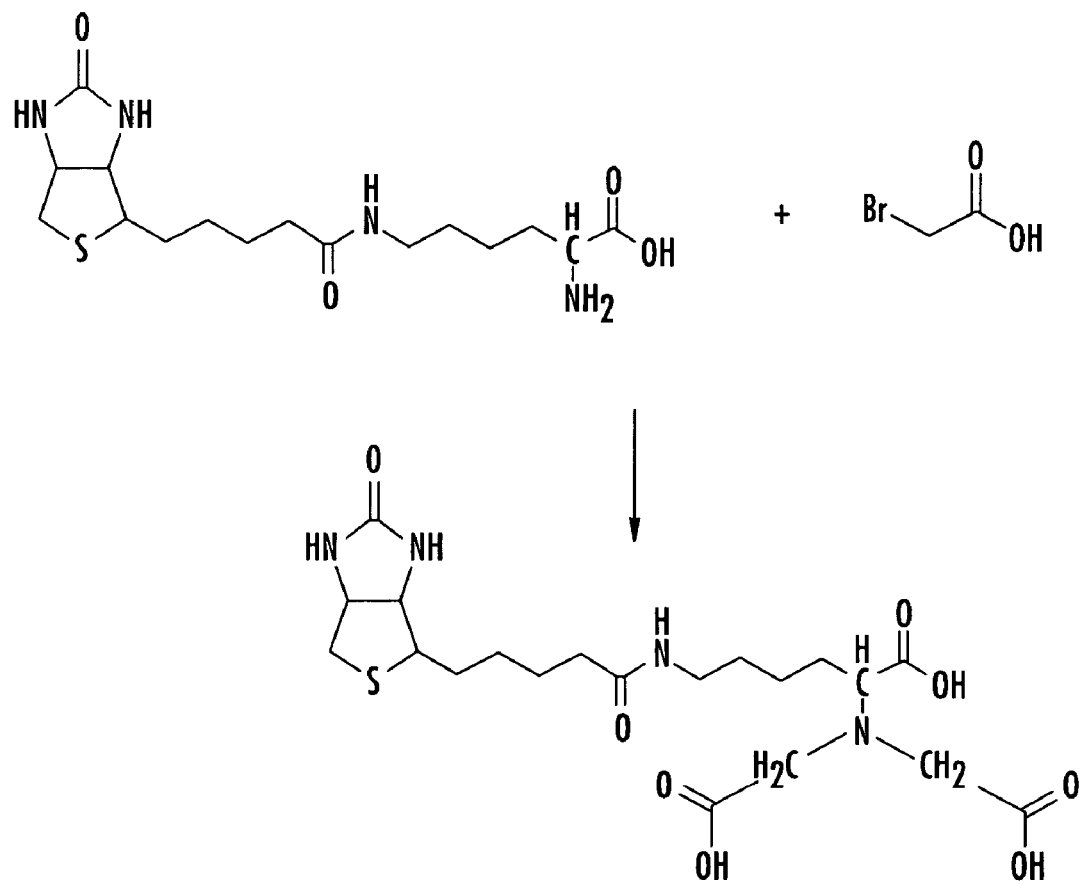
FIG. 6 depicts the synthesis of biotin-NTA according to McMahan & Burgess, 1996. A solution of biocytin (top left) is added dropwise to a cooled solution of bromoacetic acid (top right). The basic solvents of both reactants catalyze the condensation into biotin-nitriloacetic acid (biotin-NTA, bottom).

Alternatively, biotin-NTA can be synthesized according to the method of McMahan & Burgess, 1996 as depicted in FIG. 6. In this method, a solution of biocytin (FIG. 6, top left) is added dropwise to a cooled solution of bromoacetic acid (FIG. 6, top right). The basic solvents of both reactants catalyze the condensation of the reactants into biotin-NTA (FIG. 6, bottom).

In one embodiment, a method for synthesizing a PPDR comprises (a) reacting a polydentate chelator donor molecule with a detectable moiety donor under conditions wherein an detectable moiety is transferred to a polydentate chelator to form a chelator-detectable moiety complex; and (b) mixing the chelator-detectable moiety complex and a metal ion-containing solution under conditions wherein the chelator-detectable moiety complex coordinates the metal ion, forming a PPDR. In one embodiment, the detectable moiety donor is present in the reacting step in a molar excess over the polydentate chelator donor molecule. In another embodiment, the chelator-detectable moiety complex and a metal ion-containing solution are present in equimolar concentrations in the mixing step.

As used herein, the term "detectable moiety donor" refers to a molecule comprising a detectable moiety that can be reacted with a polydentate chelator donor to produce a chelator-detectable moiety complex.

Figure 7:
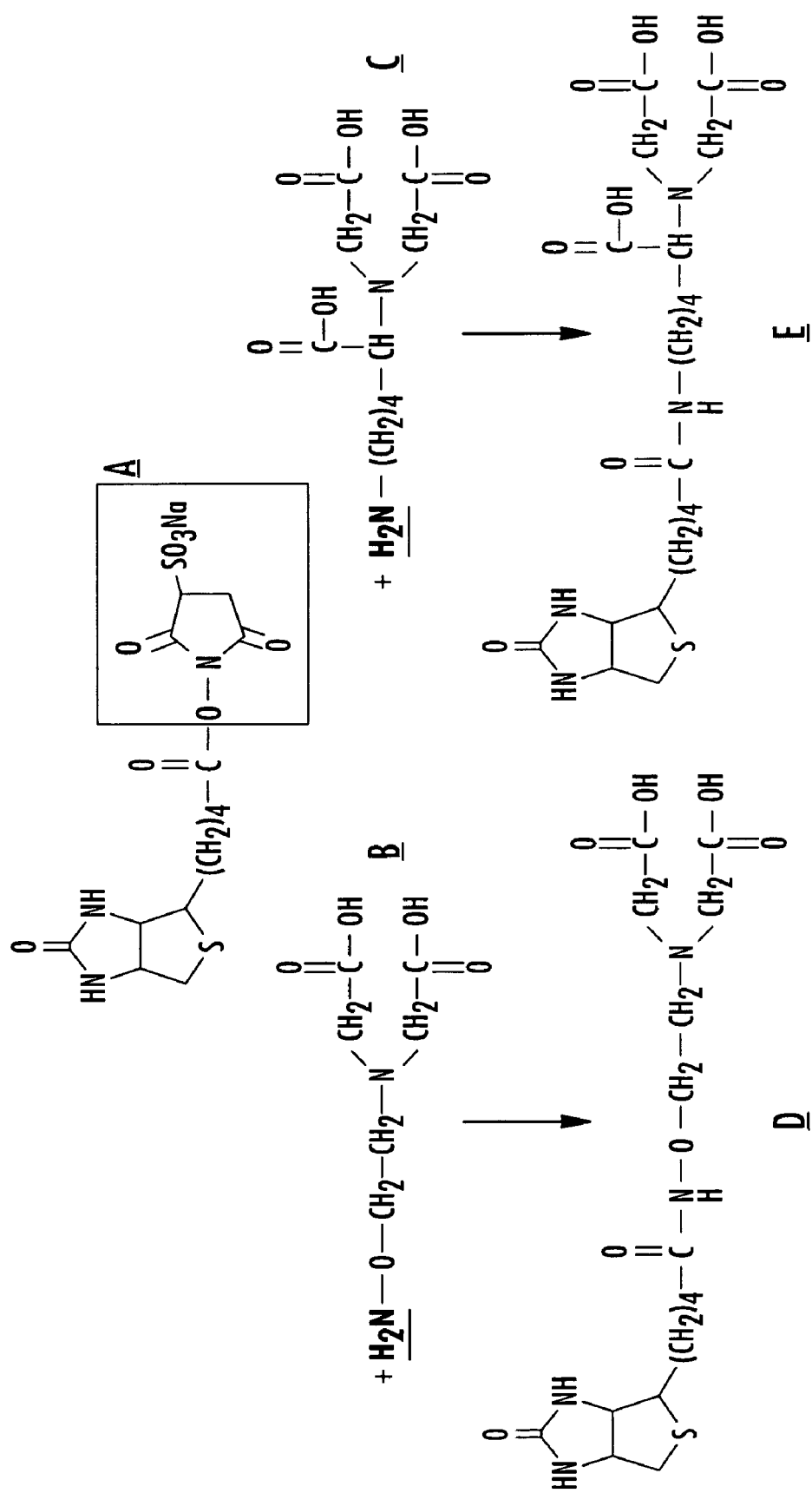
FIG. 7 depicts the synthetic reactions for biotin-IDA and biotin-NTA. Sulfo-NHS-biotin (A), a commercially available, water-soluble biotinylation reagent reacts with primary amines to form biotinyl-amide conjugates (the NHS leaving group is boxed). Reaction with the amine groups (shown in bold and underlined in B and C) of 2-(aminooxyethyl)iminodiacetic acid (AIDA; B) or aminobutyl-nitriloacetic acid (AB-NTA; C) results in the formation of biotin-IDA (D) or biotin-NTA (E), respectively. Note that biotin-X-NTA, which differs from (E) by having a flexible spacer of ~9 Å between the side-chain carbonyl and the amide nitrogen, and the analogous biotin-X-IDA, can be synthesized using sulfo-NHS-LC-biotin (available from Pierce Biotechnology, Inc., Rockford, Ill., United States of America), which includes the same spacer between the side-chain carbonyl and the NHS leaving group.

As used herein, the terms "polydentate chelator donor" and "chelator donor" are used interchangeably and refer to a molecule comprising a polydentate chelator that can be reacted with a detectable moiety donor to form a chelator-detectable moiety complex. In one embodiment, the chelator donor is selected from the group consisting of 2-(aminooxyethyl)iminodiacetic acid (AIDA), aminobutyl-nitriloacetic acid (AB-NTA), and iminodiacetic acid (IDA). In one embodiment, the detectable moiety donor is selected from the group consisting of sulfo-N-hydroxysuccinimidyl-biotin (sulfo-NHS-biotin), sulfo-NHS-LC-biotin, sulfo-NHS-LC-LC-biotin, and penta-fluorophenyl-biotin. FIG. 7 shows methods of synthesizing biotin-IDA and biotin-NTA using sulfo-NHS-biotin as the detectable moiety donor and AIDA or antibody-NTA as the chelator donor, respectively.

Figure 8:
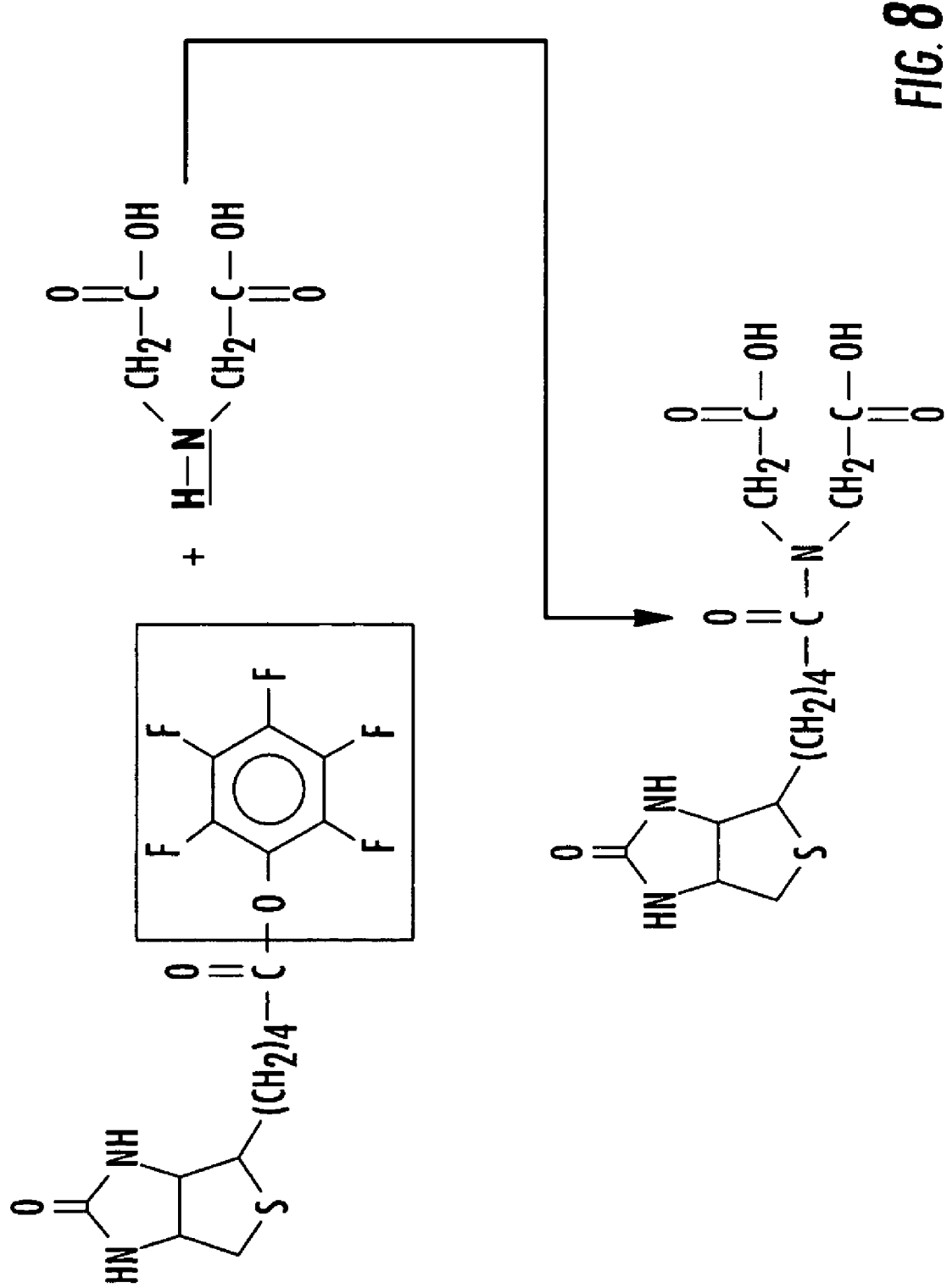
FIG. 8 depicts an alternate reaction for synthesis of biotin-IDA. Penta-fluorophenyl-biotin (PFP-biotin; top left), a commercially available biotinylation reagent that reacts with both primary and secondary amines to form biotinyl-amide conjugates (the PFP leaving group is boxed). Reaction with the secondary amine (shown in bold and underlined) of iminodiacetic acid (IDA; top right) results in the formation of biotin-IDA (bottom).

Biotin-IDA can be synthesized as shown in FIG. 8. In this reaction, penta-fluorophenyl-biotin (PFP-biotin; Pierce Biotechnology, Inc., Rockford, Ill., United States of America; FIG. 8, top left) is reacted with iminodiacetic acid (IDA; Hampshire Chemical Corp., Lexington, Mass., United States of America) to form biotin-IDA. In FIG. 8, the PFP leaving group is boxed and the reactive secondary amine is shown in bold and underlined.

I.D. PPDR Kits

In one embodiment, the presently claimed subject matter provides a kit comprising a PPDR. In another embodiment, the kit comprises a PPDR and instructions for its use. In yet another embodiment, the kit further comprises secondary reagents for use with the PPDR. Typically, the kit comprises one or more containers that hold the reagent(s).

II. Methods of Using a PPDR

II.A. Method for Detecting a Phosphoprotein

In one embodiment, the presently claimed subject matter provides a method for detecting a phosphoprotein, which comprises: (a) obtaining a protein-containing solution; (b) separating the proteins present in the solution from each other; (c) contacting the proteins with a reagent under conditions wherein the reagent will selectively bind to a phosphorylated amino acid residue present within the proteins to form a reagent/amino acid complex, wherein the reagent comprises a chelator-metal ion moiety and a detectable moiety conjugated to the chelator-metal ion moiety, wherein the chelator-metal ion moiety selectively binds to a phosphorylated amino acid residue in a phosphoprotein if present to create a chelator-metal ion-phosphoprotein (CMPP) complex, and the detectable moiety allows the CMPP complex to be detected if present; and (d) detecting the reagent/amino acid complex, wherein the detection of the reagent/amino acid complex detects a phosphoprotein.

As used herein, a "protein-containing solution" refers to a solution comprising proteins, in which the presence of phosphoproteins is to be assayed. In one embodiment, a protein-containing solution is a cell lysate. As used herein, the term "cell lysate" refers to a solution that contains all or nearly all of the proteins found with a cell. A cell lysate can be produced by methods that are well known in the art, such as by incubating the cells under appropriate conditions in a lysis buffer. A lysis buffer usually comprises a detergent that serves to disrupt the cell membrane. For example, a representative lysis buffer is 50 mM Tris-HCl, pH 7.5, 150 mM NaCl, 1% Nonidet P40, and 0.5% sodium deoxycholate. Lysis buffers can also include commercially available protease inhibitors such as leupeptin, pepstatin, aprotinin, and combinations of these (available from Roche Applied Science, Indianapolis, Ind., United States of America).

In accordance with the methods of the presently claimed subject matter, the proteins in the protein-containing solution are separated.

As used herein, the term "separating" refers to a process of organizing the proteins that comprise a protein-containing solution based upon a characteristic such as molecular weight, charge, antigenicity, or other feature for which a separation technique is available. Electrophoresis techniques can be performed, for example. Chromatographic separation can also be employed. In one embodiment of the presently claimed subject matter, the proteins of a protein-containing solution are separated by SDS-PAGE. In another embodiment, the proteins of a protein-containing solution are separated by 2-DE. The separated proteins are then contacted with a reagent that allows phosphoproteins present within the protein-containing solution to be detected.

As used herein, the terms "contacting" and "contacted" refer to a set of conditions under which two molecules are brought into proximity in such a way that binding between the two can occur. In one embodiment, the presently claimed subject matter involves contacting a reagent with a phosphoprotein. In one embodiment, the reagent is a PPDR comprising a chelator-metal ion moiety with a conjugated detectable moiety. The contacting step can be performed with the reagent and phosphoprotein both in solution, or with the phosphoprotein immobilized on a solid support. As used herein, the term "solid support" means a non-aqueous matrix to which a target protein can adhere. Exemplary solid phases include, but are not limited to a glass, silica, polymeric, nitrocellulose, carbohydrate, and PVDF surfaces. The solid support can comprise a purification column or a discontinuous phase of discrete particles. In one embodiment, a solid support is a PVDF membrane.

In one embodiment of the presently claimed subject matter, the proteins present in a cell lysate are separated by 2-DE, transferred to a PVDF membrane, and the contacting is accomplished by adding an aqueous solution comprising a PPDR under conditions wherein the reagent will selectively bind to a phosphoamino acid present in a protein immobilized on the PVDF membrane. As used herein, the terms "conditions wherein the reagent will selectively bind" and "permissive conditions" refer to a set of conditions that allow a PPDR to selectively bind to a phosphoamino acid residue present in a phosphoprotein. In one embodiment, the conditions wherein the reagent will selectively bind to a phosphorylated amino acid residue present within the immobilized proteins to form a reagent/amino acid complex comprise permissive conditions, followed by washing the solid support to remove unbound reagent. In one embodiment, permissive conditions include performing the contacting step at pH between about 5.0 and 7.0 and the washing step at a pH between about 6.9 and 9.5. Representative contacting step pHs include, but are not limited to about 5.0, about 5.2, about 5.4, about 5.6, about 5.8, about 6.0, about 6.2, about 6.4, about 6.6, about 6.8, and about 7.0. Representative washing step pHs include, but are not limited to about 6.9, about 7.1, about 7.3, about 7.5, about 7.7, about 7.9, about 8.1, about 8.3, about 8.5, about 8.7, about 8.9, about 9.1, about 9.3, and about 9.5. Representative values for salt concentration include but are not limited to 0.0 M, 0.1 M, 0.25 M, 0.5 M, 0.75 M, 1.0 M, 1.25 M and 1.5 M, and any value there between.

For example, contacting can occur in a buffer comprising 50 mM PIPES-HCl, pH 6.5, and 1 M NaCl, and washing can occur in a buffer comprising 50 mM Tris-HCl, pH 8.5, and 1 M NaCl. It is to be understood that just as pH differences can alter the nature of the contacting and washing steps, so too can the concentration of cation in the buffers in which these steps take place. Upon review of the present disclosure, one of ordinary skill in the art will understand how to manipulate the pH and salt concentrations in order to optimize the signal-to-noise ratio in the detection method.

Figure 5:
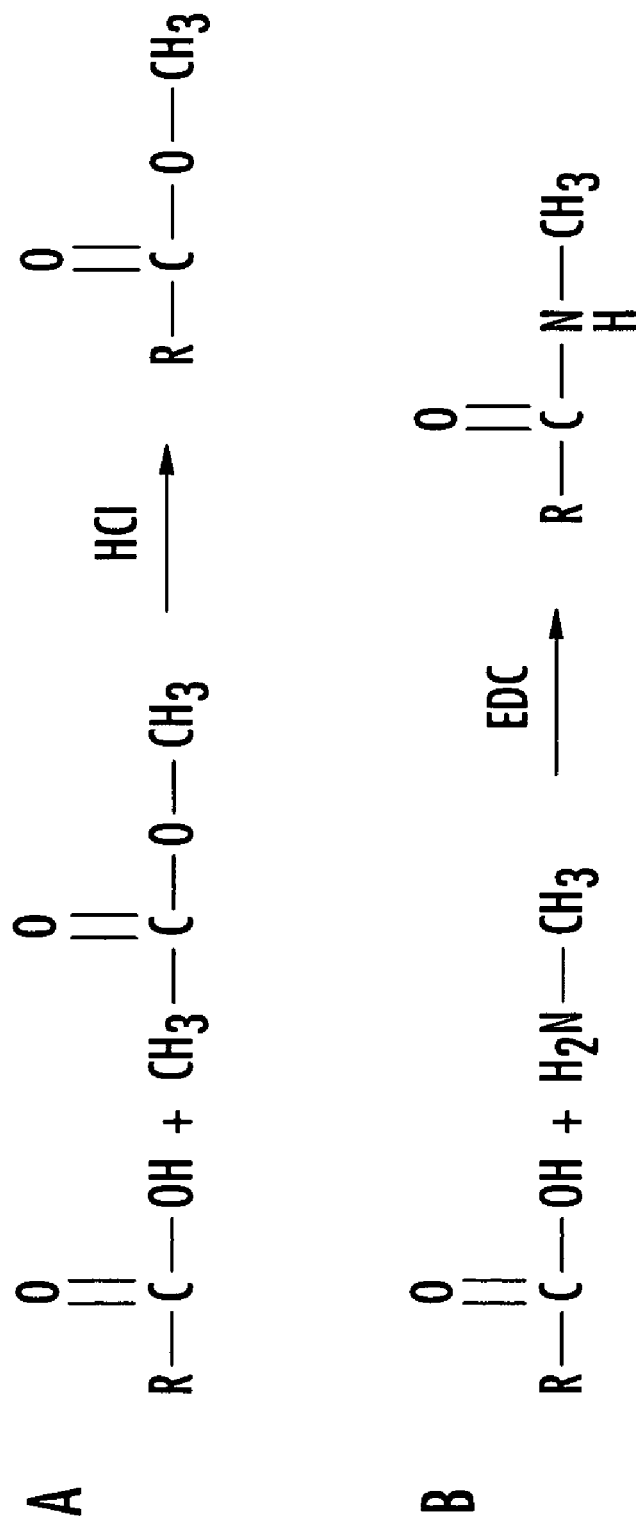
FIGS. 5A and 5B depict strategies for blocking carboxylic acid groups.

In one embodiment, the immobilized proteins are treated with a carboxy-blocking reagent after the separating step and prior to the contacting step. As used herein, the term "carboxy-blocking" refers to a process by which carboxyl groups that are present in the amino acids aspartic acid and glutamic acid are modified so that they do not react with the PPDR. Carboxy-blocking can be accomplished by conversion of carboxy groups to carboxymethyl esters by treatment with methanolic HCl (as shown in FIG. 5A). Alternatively, carboxy-blocking can be accomplished by using the chemical cross-linker EDC (N-ethyl-N'-(3-(dimethyl-aminopropyl) carbodiimide HCl), which reacts with carboxylic acid groups to form a reactive, O-acylurea intermediate that, in turn, reacts with primary amines to form an amide bond (see FIG. 5B). EDC thus modifies acidic groups with small organic primary amines to form "capped" residues that are non-reactive with SoMACs. And finally, N-ethyl-5-phenylisoxazolium-3'-sulfate (also known as Woodward's Reagent "K"; available from Sigma, St. Louis, Mo., United States of America) has been used to modify acidic residues in proteins. Sinha & Brewer, 1985; Johnson & Dekker, 1996; Paoli et al., 1997; Yang et al., 1999; Verri et al., 2002. In one embodiment, the carboxy-blocking reagent is selected from the group consisting of methanolic HCl, a carbodiimide, and Woodward's Reagent "K".

II.B. Method for Detecting a Change in Phosphorylation Status

A representative approach for detecting a change in phosphorylation status of the phosphoproteome of a cell is depicted in FIG. 1. Cell lysates are prepared from cells "before" and "after" a change in state of the cell (FIG. 1A). The proteins present in each lysate are then separated by 2-DE (FIG. 1B) and phosphoproteins are detected (FIG. 1C). Differences between the phosphorylation states of the proteins present in the lysates are identified by comparing the proteins detected in the "before" sample with those detected in the "after" sample (FIG. 1D). Those proteins for which a difference was detected can then be subjected to further analysis, for example, by mass spectroscopy (MS).

Thus, in one embodiment, the presently claimed subject matter involves a method for detecting a change in phosphorylation status of a protein present within a target tissue in response to a change in state. The method can comprise: (a) obtaining a protein lysate from a cell from the target tissue prior to the change in state; (b) separating the proteins present in the lysate from each other; (c) contacting the proteins with a reagent comprising a chelator-metal ion moiety and an detectable moiety conjugated to the chelator-metal ion moiety, wherein the chelator-metal ion moiety selectively binds to a phosphorylated amino acid residue in a phosphoprotein if present to create a chelator-metal ion-phosphoprotein (CMPP) complex, and the detectable moiety allows the CMPP complex to be detected if present, under conditions wherein the reagent will selectively bind to a phosphorylated amino acid residue present within the proteins to form a reagent/amino acid complex; (d) detecting the reagent/amino acid complex, wherein the reagent/amino acid complex is indicative of a phosphoprotein in the cell lysate; (e) creating a profile indicative of the detected phosphoproteins of the lysate; (f) obtaining a protein lysate from a cell from the target tissue after the change in state; (g) repeating steps b) through e) for the lysate from a cell from the target tissue after the change in state; and (h) comparing the profile from the lysate from the cell from the target tissue prior to the change in state to the profile from the lysate from the cell from the target tissue after the change in state, wherein a difference between the two profiles is indicative of a change in the phosphorylation status of a protein present within the target tissue in response to the change in state of the target tissue.

As used herein, the term "a change in phosphorylation status" refers to a difference in phosphorylation of a protein before and after a certain biochemically relevant event. This difference can be either qualitative or quantitative. This change in phosphorylation status can result from the normal biochemical processes that occur within a cell, most notably via the actions of cellular kinases and phosphatases.

As used herein, the term "biochemically relevant event" refers to any external or internal stimulus that causes a change in the phosphoproteome of a cell. A biochemically relevant event includes, but is not limited to the binding of a growth factor to its receptor, a change from a pre-neoplastic to a neoplastic state, a change from a benign to a malignant state, and a change from a quiescent to a proliferative or differentiated state. A biochemically relevant event also includes any change in the environment of a cell that results in changes to the phosphoproteome. Such environmental changes include conditions that result in the induction of stress-response pathways, including but not limited to hypoxia response pathways, heat or cold response pathways, and apoptotic pathways.

The term "target tissue" refers to any cell or group of cells. This term includes single cells and populations of cells. The term includes cells that are being grown in vitro as well as cells that are present in an organism in vivo. As such, the term includes, but is not limited to cultured cells as well as cell populations comprising glands and organs such as skin, liver, heart, kidney, brain, pancreas, lung, stomach, and reproductive organs. It also includes, but is not limited to mixed cell populations such as bone marrow. Further, it includes, but is not limited to such abnormal cells as neoplastic or tumor cells, whether individually or as a part of solid or metastatic tumors.

As used herein, the term "change in state" refers to a change in a cell from one condition to another. A change in state can result from the application of external stimulus, including, but not limited to the binding of a growth factor. Alternatively, a change in state can result from an internal stimulus. For example, a change in state can occur as a result of a genomic mutation. Such a mutation includes, but is not limited to a mutation that inactivates a tumor suppressor or activates a cellular oncogene. In one embodiment, the change in state is from a non-neoplastic to a neoplastic state. In another embodiment, the change in state is from a non-differentiated to a differentiated state. In another embodiment, the change in state is from a benign to a malignant state. In yet another embodiment, the change in state is from an unstimulated to a stimulated state.

As used herein, "non-neoplastic" is to be contrasted with "neoplastic". The term "neoplastic" is intended to refer to its ordinary meaning, namely aberrant growth characterized by abnormally rapid cellular proliferation. In general, the term "neoplastic" encompasses growth that can be either benign or malignant, or a combination of the two. "Non-neoplastic", therefore, refers to a growth state that is part of the normal growth and differentiation of a cell or group of cells.

As used herein, "non-differentiated" is to be contrasted with "differentiated". The term "differentiated" is intended to refer to its ordinary meaning. A "differentiated" cell, therefore, is one that has undergone differentiation such that it is restricted in the type of cell that it can become. The term "differentiated" is intended to encompass a cell that is terminally differentiated, for example a muscle cell or a neuron, as well as a cell that is partially differentiated, such as a somatic stem cell. As such, the terms "differentiated" and "non-differentiated" are to be understood as relative, in that along a particular differentiation pathway (for example, from a totipotent stem cell to an erythrocyte), cells will be considered alternatively differentiated or non-differentiated depending on their relationship to each other. By way of illustration, a reticulocyte would be considered non-differentiated when compared to an erythrocyte, but differentiated when compared to a normoblast.

As used herein, "benign" is to be contrasted with "malignant". The terms "benign" and "malignant" are intended to convey their ordinary meaning. Therefore, "malignant" is intended to refer to an abnormal growth state that is characterized by invasive growth causing destruction of local tissues and cells, often leading to metastasis and death. In contrast, "benign" is intended to refer to an abnormal growth state wherein the growth does not result in the invasion of the local tissue, metastasis, or death. As used herein, "benign" is also intended to refer to an abnormal growth state of a cell or group of cells prior to the biochemical alterations that cause the cell or group of cells to become malignant.

As used herein, "unstimulated" is to be contrasted with "stimulated". These terms are intended to be understood in relation to each other, such that an unstimulated cell is one that has not been exposed to a particular stimulus. Stimuli that can be employed in the embodiments of the instant presently claimed subject matter include, but are not limited to heat, light, chemicals, growth factors, hormones, nutrients, water, or combinations of these. For example, an unstimulated cell can be a vascular endothelial cell that expresses a membrane-bound vascular endothelial growth factor receptor. Upon binding of vascular endothelial growth factor to the cell, this cell can become a stimulated cell.

As used herein, the term "profile" refers to a catalog of the phosphoproteome of a cell. As such, a profile includes all the proteins that are phosphorylated in a given cell under a given set of conditions. Profiles allow the phosphoproteome of a cell to be compared under different conditions. For example, comparing the profiles of a cell before and after exposure to a growth factor allow for the determination of which proteins experience phosphorylation changes as a result of treatment with that growth factor. As an additional example, comparing the profiles of a cell before and after a change from a non-neoplastic to a neoplastic phenotype, or before and after a change from benign to malignant growth can be used to identify candidate proteins that contribute to the given changes. The identification of proteins that undergo phosphorylation changes as cells undergo changes in state can lead to the identification of potential targets for therapeutic intervention.

II.C. Method for Early Diagnosis of a Change in State of a Target Tissue

In one embodiment, the presently claimed subject matter involves a method for early diagnosis of a change in state of a target tissue. The method can comprise: (a) detecting a phosphorylation state of a protein in a target tissue; and (b) comparing the detected phosphorylation state of the protein to a standard profile, wherein the comparison identifies a change in state of the target tissue. The presently claimed subject matter envisions building profiles of the phosphoproteomes of cells before and after medically relevant changes in state. Comparisons of phosphoproteomes can allow for the identification of changes in the phosphorylation state of specific proteins that are indicative of the given change in state. As such, it should be possible to correlate such changes with the change of state prior to the appearance of other characteristics of the cell that would indicate that the cell has changed state.

EXAMPLES

The following Examples have been included to illustrate modes of the presently claimed subject matter. Certain aspects of the following Examples are described in terms of techniques and procedures found or contemplated by the present inventor to work well in the practice of the presently claimed subject matter. These Examples illustrate standard laboratory practices of the inventor. In light of the present disclosure and the general level of skill in the art, those of skill will appreciate that the following Examples are intended to be exemplary only and that numerous changes, modifications, and alterations can be employed without departing from the scope of the presently claimed subject matter.

Example 1

Synthesis of a PPDR

Biotin-X-NTA was mixed with 100 mM stocks of either $Fe(NO_3)_3$, $GaCl_3$, or $AlCl_3$ at equal molar concentrations (30 µM), then diluted 1:10 in binding buffer (50 mM PIPES-HCl, pH 6.5 and 1 M NaCl). The diluted sample was mixed with streptavidin-conjugated horseradish peroxidase (sA-HRP; Amersham Biosciences, Piscataway, N.J., United States of America) at a 1:5000 dilution.

Example 2

Detection of Phosphorylated Nck

Figure 3:
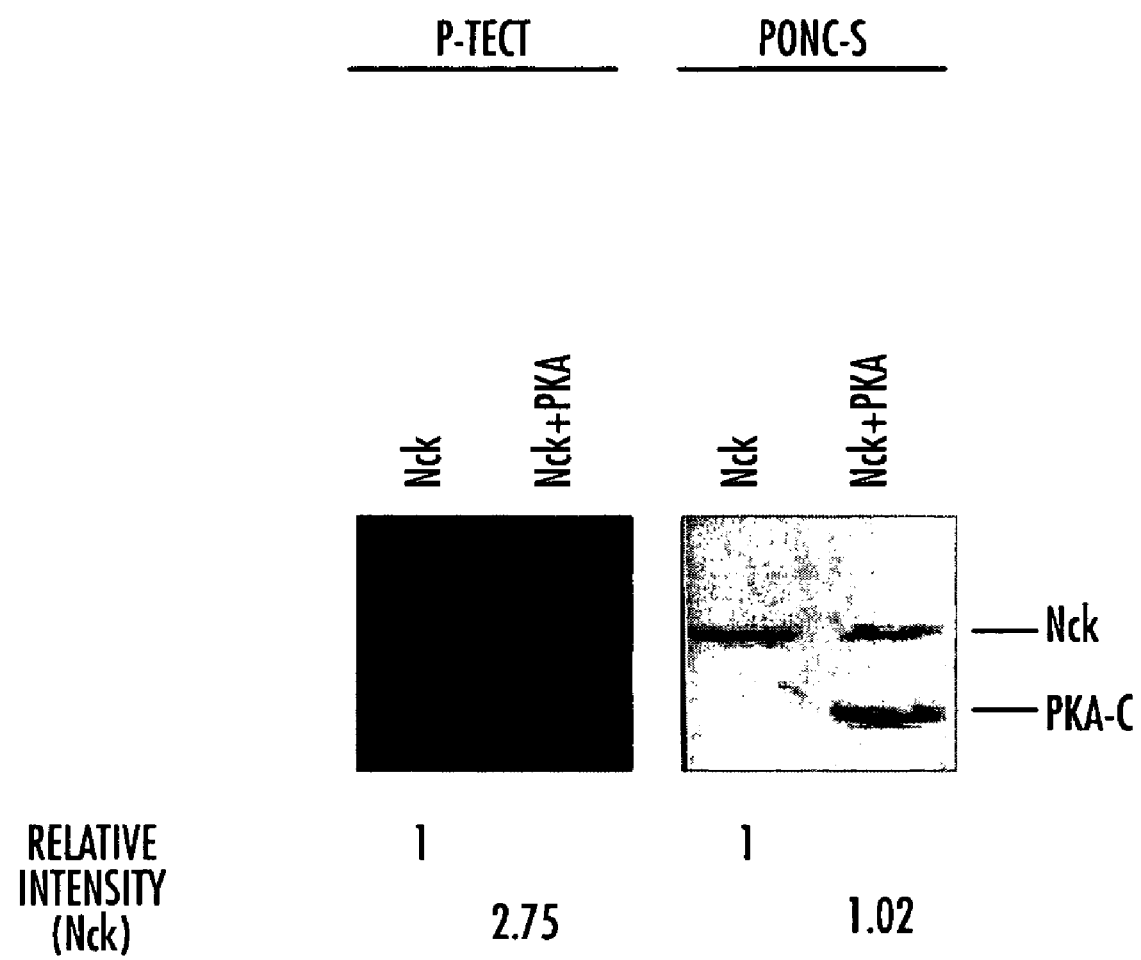
FIG. 3 depicts the detection of PKA-mediated phosphorylation of Nck using a phosphoprotein detection reagent. Purified, recombinant Nck (0.2 μg) was incubated in phosphorylation buffer alone (Nck) or buffer containing purified PKA catalytic subunit (Nck+PKA) for 30 minutes at 30° C. Reactions were stopped with sample buffer and proteins were separated by SDS-PAGE and transferred to PVDF. The dried membrane was re-wet and incubated for 1 hour with methanolic HCl to block cross-reactive carboxy groups, washed extensively, then incubated with a mixture of a phosphoprotein detection reagent (final concentration=5 μg/ml), $FeCl_3$ (final concentration=3 μM), and streptavidin-conjugated horseradish peroxidase (HRP) (1:5000 dilution) for 1 hour. Phosphoprotein detection reagent (P-Tect) reactivity was determined by enhanced chemiluminescence, while equal loading was confirmed by staining the washed blot with Ponceau-S (Ponc S).

Preliminary experiments utilized purified proteins to facilitate interpretation of initial results. Specifically, purified recombinant Nck, an adapter protein and known substrate for the cAMP-dependent protein kinase A (PKA; McCarty, 1998; Li & She, 2000), was used as a test target to determine whether its phosphorylation could be detected using a SoMAC approach. Nck was expressed as a fusion with glutathione-S-transferase (GST) in bacteria transformed with the plasmid pGEX2T-Nck (a gift of Dr. Lawrence Quilliam, Indiana University, United States of America), initially purified by FPLC over glutathione-sepharose (Amersham Biosciences Corp., Piscataway, N.J., United States of America), and released and separated from GST by thrombin cleavage and Mono-Q FPLC. Purified Nck was phosphorylated by incubation with purified PKA catalytic subunit (New England Biolabs, Beverly, Mass., United States of America) and ATP, separated by SDS-PAGE and transferred to PVDF membrane. Buffer conditions for membrane blotting were made to mimic those previously described for separation of phosphoproteins by IMAC (Andersson & Porath, 1986; Muszynska et al., 1986; Muszynska et al., 1992), namely high salt and mildly acidic pH. Thus, binding buffer included 50 mM PIPES-HCl (pH 6.5) and 1M NaCl. Biotin-X-NTA and $Fe(NO_3)_3$ were pre-mixed at equal molar concentrations (30 µM), then diluted 1:10 in binding buffer and mixed with streptavidin-conjugated horseradish peroxidase (sA-HRP, Amersham Biosciences Corp., Piscataway, N.J., United States of America) that had been dialyzed against 50 mM PIPES (pH 6.5)/150 mM NaCl. As shown in FIG. 3, $Fe^{3+}$-coordinated biotin-X-NTA showed strong reactivity with phosphorylated Nck.

Example 3

Detection of Reversible Nck Phosphorylation $Fe^{3+}$-coordinated biotin-X-NTA showed strong reactivity with phosphorylated Nck, but reacted equally with unphosphorylated Nck. See FIG. 3. While binding to phosphorylated Nck was increased, there was also detectable binding to purified Nck incubated without PKA and to PKA.

Figure 4:
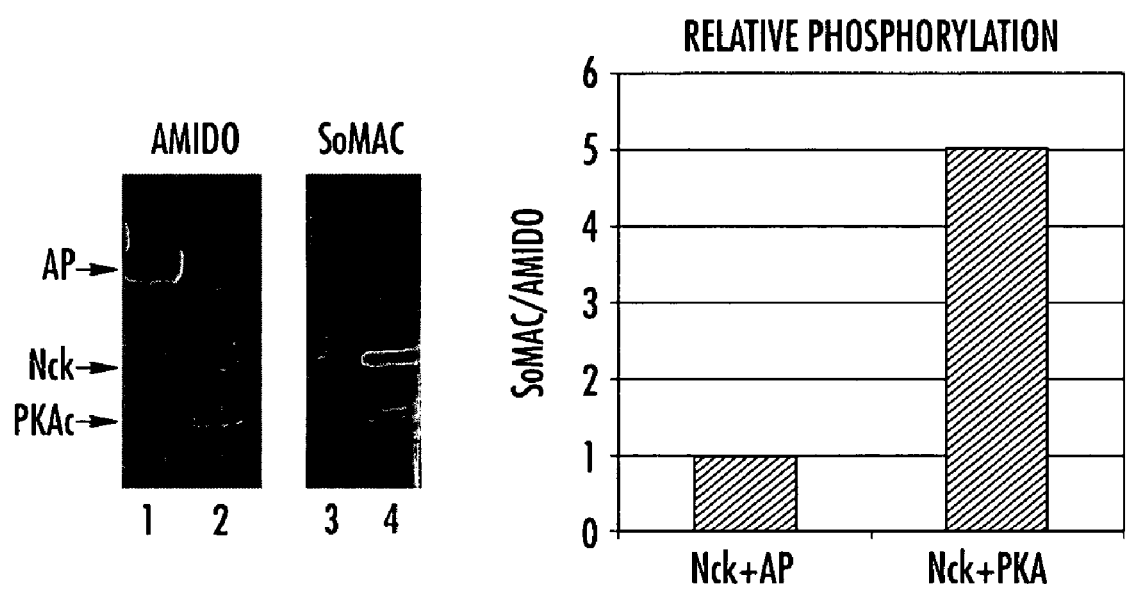
FIG. 4 depicts the detection of reversible Nck phosphorylation with phosphoprotein detection reagent. Purified Nck was phosphorylated by PKA catalytic subunit (PKAc; lanes 2 and 4) or phosphorylated, re-purified, and dephosphorylated with alkaline phosphatase (AP; lanes 1 and 3). Reactions were separated by SDS-PAGE and transferred to PVDF membrane, which was then stained with Amido Black, destained, and probed with phosphoprotein detection reagent (SoMAC) as in FIG. 3. The graph shows normalized, relative Nck phosphorylation in the two samples.

In an attempt to address whether this binding represents residual cross-reactivity with something other than phosphate or, perhaps, detection of some phosphorylation event that occurs within the bacteria during expression, Nck was re-purified after phosphorylation by PKA and either left untreated or incubated with purified alkaline phosphatase (AP; New England Biolabs, Beverley, Mass., United States of America) to remove added phosphates. Both forms were analyzed as shown in FIG. 4.

Purified Nck was phosphorylated by PKA catalytic sub-unit. Another sample of purified Nck was phosphorylated, re-purified, and dephosphorylated with alkaline phosphatase. The samples were run in individual lanes of an SDS-PAGE gel, transferred to a PVDF membrane, and probed with the PPDR as in Example 2. As shown in FIG. 4, the PPDR detected phosphorylated Nck (FIG. 4, left panel, lanes 2 and 4). Though some reactivity towards dephosphorylated Nck still remained, it was five-fold lower than towards the phosphorylated form, reinforcing the notion that a significant portion of the reactivity was due to Nck phosphorylation. Interestingly, there was no reactivity with AP, even though AP was present on the blot in at least 20-fold molar excess over Nck. This suggests that the residual binding to Nck is idiotypic for that protein (or proteins possessing some similar physico-chemical property) and that the PPDR does not have appreciable cross-reactivity to proteins in general. It is interesting to note that Nck does have a number of poly-Glu/Asp regions in its sequence, and therefore may require more thorough blocking of these residues. Purified Nck was phosphorylated by PKA catalytic subunit. Another sample of purified Nck was phosphorylated, re-purified, and dephosphorylated with alkaline phosphatase. The samples were run in individual lanes of an SDS-PAGE gel, transferred to a PVDF membrane, and probed with the PPDR as in Example 2. As shown in FIG. 4, the PPDR detected phosphorylated Nck (FIG. 4, left panel, lanes 2 and 4).

Example 4

Optimization of Buffer Conditions

The binding of metal ion chelates to phosphorylated ligands is dependent on pH, with acidic conditions favoring binding and basic conditions allowing desorption. The conditions reported for phosphate-mediated binding to IMAC columns range from pH 5.0 to 7.0, while reported elution conditions overlap at pH 6.9 to 9.5. Importantly, the non-specific binding of non-phosphorylated species increases at lower pH values and is minimized or eliminated with increasing pH. Thus, the ideal pH for PPDR binding buffer is low enough to promote and retain specific binding to phosphates but high enough to minimize or eliminate non-specific binding. Preliminary studies used a PIPES-based buffer at pH 6.5 with reasonable results, so this value serves as a starting point around which other experiments are performed. Using MES, PIPES, and Tris, a panel of buffers ranging in pH from 5.0 to 7.5, all containing 1M NaCl, are used as binding and washing buffers for PPDR-based detection of purified Nck, PKA-phosphorylated Nck, phosphorylase B, and phosphorylase A. Detection is carried out on membranes with and without blocking of carboxylic acids by methanolic HCl, to determine whether variations in pH can overcome non-specific binding and obviate the need for blocking. The relative reactivity of SoMAC with phosphorylated and unphosphorylated species is visualized by chemiluminescence, quantitated by densitometry, and compared between buffer conditions.

Example 5

Carboxy-Blocking Variations

Because of similarities between oxygen-rich, negatively charged phosphate groups and carboxylic acid groups, phosphate-binding IMAC resins have been shown to retain proteins or peptides rich in acidic residues, especially when those residues are clustered. Although this binding is typically weak compared to phosphate binding, the potential cross-reactivity of metal ion chelates with moieties other than phosphate presents a concern in the use of PPDRs for phosphoprotein detection. At least part of this cross-reactivity can be addressed by altering the metal ion (e.g. $Ga^{3+}$ rather than $Fe^{3+}$) and/or optimizing buffer pH, as higher pH values favor phosphate-selective binding as discussed in Example 4. It is possible that cross-reactivity will not be completely eliminated by modification of binding conditions alone. In this case, the binding to carboxylic acids are eliminated by derivatization of the acidic groups using a carboxylic acid-specific chemistry.

Methanolic HCl

Carboxylic acid groups of Asp, Glu, and carboxy-terminal residues react with anhydrous, methanolic HCl to form carboxymethyl esters (FIG. 5a), a reaction used with success to eliminate carboxylic acid-mediate cross-reactivity with phosphate-selective IMAC columns. Methanolic HCl is prepared by careful, drop-wise addition of acetyl chloride to stirring, anhydrous methanol (at 160 µl per ml). Alternatively, pre-measured 'kits' for preparation are also available (Sigma, St. Louis, Mo., United States of America). The methanolic HCl method of blocking carboxylic acid groups is particularly amenable for adaptation to proteins immobilized on PVDF membranes, as PVDF is routinely pre-wetted with anhydrous methanol prior to wetting in aqueous transfer or blotting buffers. Thus, membranes that have been dried after protein transfer are submerged slowly in freshly-prepared methanolic HCl and incubated at room temperature for 2 hours. This method of carboxymethylation is effective in increasing the signal-to-noise ratio of PPDR binding to phosphorylated proteins.

Reaction with Carbodiimides

The chemical cross-linker EDC (N-ethyl-N'-(3-(dimethylaminopropyl)carbodiimide HCl) reacts with carboxylic acid groups to form a reactive, O-acylurea intermediate that, in turn, reacts with primary amines to form an amide bond. EDC is used to modify acidic groups with small organic primary amines, forming 'capped' residues that would be non-reactive with PPDRs (FIG. 5b). PVDF membranes containing a panel of phosphorylated and non-phosphorylated proteins are immersed in a volume of 50 mM MES (pH 6) containing various concentrations of EDC (5-50 mM) and an excess of a small organic amine (e.g. 100 mM methylamine, ethylamine, or diaminomethane) and incubated at room temperature for various periods of time. Unreacted carbodiimide are removed by extensive, sequential washing with MES+100 mM methylamine (or equivalent) and PPDR binding buffer. Blocked membranes and control membranes (incubated and washed in buffers without EDC) are then probed with PPDR and sA-HRP. If needed, other carbodiimides with demonstrated selectivity for carboxylic acid groups on proteins (e.g. 1-cyclohexyl-3-(2-morpholinoethyl)carbodiimide metho-p-toluenesulfonate) are also tested in similar fashion.

Woodward's Reagent K

This compound, also known as WRK or N-ethyl-5-phenylisoxazolium-3'-sulfate (available from Sigma, Rockford, Ill., United States of America), has been used for a number of years to modify acidic residues in proteins. To test the ability of WRK to reduce PPDR cross-reactivity, PVDF membranes containing separated proteins and phosphoproteins are incubated in buffer containing 100 mM MES, pH 6, and various concentrations of WRK (0-500 µM, diluted from a 20 mM stock made in 1 mM ice-cold HCl) for various periods of time (5 to 30 minutes), then washed as described above for carbodiimide reactions.

Example 6

Detection of Phosphorylated Nck Subsequent to Carboxy-Blocking

In order to test if blocking potentially reactive oxygen-rich carboxylic acid groups of Asp and Glu residues improves the efficiency of detecting phosphorylated Nck, a carboxy-blocking step was added using methanolic HCl prior to detection with a PPDR. Recombinant Nck was produced, phosphorylated, and separated by SDS-PAGE as described in Example 1. The separated proteins were then transferred to a PVDF membrane and air-dried. Methanolic HCl was freshly prepared by drop-wise addition of acetyl chloride to anhydrous methanol according to Ficarro et al., 2002. The air-dried membrane was re-wetted and soaked in the methanolic HCl solution for 1 hour at room temperature. After extensive washing in binding buffer, the membrane was incubated with Fe-loaded SoMAC and sA-HRP as described above, then developed by enhanced chemiluminescence. Under these new conditions, a significant difference in SoMAC binding to phosphorylated versus unphosphorylated Nck was observed (FIG. 3). Specifically, incubation of Nck with PKA causes a three-fold increase in PPDR reactivity. There was also significant reactivity with the band corresponding to the catalytic subunit of PKA, which is known to autophosphorylate. Smith et al., 1999.

Example 7

Sensitivity and Specificity of Detection

Decreasing amounts (500 ng-500 pg) of a known phosphoprotein (e.g. phosphorylase A or PKA-phosphorylated Nck) are run on SDS-PAGE gels, transferred to PVDF, carboxy-blocked (if needed), and probed with PPDR and sA-HRP. Reactivity/binding are assessed by chemiluminescence followed by densitometry and plotted as function of amount of protein. The sensitivity of PPDR binding to a given phosphorylated protein can depend on the stoichiometry of phosphorylation of that protein. Thus, plots generated from different phosphoproteins with known phosphate content are compared. Side-by-side comparisons of a singly-phosphorylated protein (e.g. phosphorylase A) with a multiply-phosphorylated protein with known (or determinable) phosphate stoichiometry are performed. The purified catalytic subunit of PKA is implemented for this in two ways. First, the purified subunit itself contains about 2 moles phosphate/mol protein from autophosphorylation on a Thr and a Ser residue. Second, PKA can be used to phosphorylate two Ser and one Thr residue in the vasodilator-stimulated phosphoprotein (VASP), giving 3 moles phosphate/mol protein. Purified PKA is available from commercial sources (e.g. New England Biolabs, Beverley, Mass., United States of America), while plasmids for expressing recombinant VASP (as a GST-fusion protein) have recently been constructed in our laboratory. VASP phosphorylation by PKA is initially performed with $^{32}P$-γ-ATP to confirm the putative stoichiometry of phosphorylation, then repeated with cold ATP for PPDR studies.

FIG. 4 indicates that PPDR shows no significant binding to over 3 µg of alkaline phosphatase. Different proteins can support different degrees of non-specific (i.e. non-phospho-specific) PPDR binding. PPDR use over time can address the characterization of 'false-positives' (i.e. proteins that are detected but not phosphorylated). This aspect of PPDR reactivity is tested by assaying differing ratios of phosphorylated to non-phosphorylated forms of phosphorylase protein, which is transferred to PVDF membranes and probed with PPDR and sA-HRP. Alternatively, a fixed amount of the phosphorylated form (e.g. 100 ng) is mixed with increasing amounts of the non-phosphorylated form (e.g. 0-2 μg) and assayed with a PPDR and sA-HRP.

The preliminary test proteins Nck and phosphorylase contain only pSer. However, PPDR also showed strong reactivity with the purified PKA catalytic subunit (see FIGS. 3 and 4), which is known to be autophosphorylated on $Thr^{197}$ and $Ser^{338}$. Thus, while pSer supports PPDR binding, pThr and pTyr remain to be directly and exclusively tested. To assay PPDR reactivity with pThr, the inhibitor-1 protein of protein phosphatase-1, a commercially-available, 31 kilodalton (kDa) protein that is phosphorylated exclusively at a single Thr residue ($Thr^{35}$) by PKA is used. For pTyr, acid-denatured enolase phosphorylated in vitro by a commercially available, purified Src (or another Src-family kinase) is used. Both targets, plus phosphorylase A and/or PKA-phosphorylated Nck, are separated by SDS-PAGE, transferred to PVDF membranes and probed with PPDR+sA-HRP. Because the binding of PPDR is mediated solely by the phosphate group without contribution of the anchoring amino acid, all three phospho-amino acids are readily detected. Other appropriate targets are also tested to determine whether the binding is universal or specific for the test proteins. A convenient alternate is VASP, which can be phosphorylated on two Ser and one Thr residue by PKA in vitro. Plasmids encoding non-phosphorylatable point mutations at each position are available, and double mutations (e.g. a double Ser→Ala mutant that leaves only the Thr remaining) can be easily introduced by standard techniques (e.g. Stratagene's Quickchange Mutagenesis Kit, Stratagene, La Jolla, Calif., United States of America).

REFERENCES

The publications and other materials listed below and/or set forth in the text above to illuminate the background of the presently claimed subject matter, and in particular cases, to provide additional details respecting the practice, are fully incorporated herein by reference.

Ahn N G & Resing K A (2001) Toward the phosphoproteome. *Nature Biotechnol* 19:317-318.

Andersson L & Porath J (1986) Isolation of phosphoproteins by immobilized metal (Fe3+) affinity chromatography. *Anal Biochem* 154:250-254.

Blume-Jensen P & Hunter T (2001) Oncogenic kinase signalling. *Nature* 411:355-365.

Cohen P (2000) The regulation of protein function by multi-site phosphorylation—a 25 year update. *Trends Biochem Sci* 25:596-601.

Cohen P (2002a) Protein kinases—the major drug targets of the twenty-first century? *Nature Rev Drug Discov* 1:309-315.

Cohen P (2002b) The origins of protein phosphorylation. *Nature Cell Biol* 4:E127-130

Conrads T P, Issaq H J & Veenstra T D (2002) New tools for quantitative phosphoproteome analysis. *Biochem Biophys Res Commun* 290:885-890.

Cooper J A, Sefton B M & Hunter T (1983) Detection and quantification of phosphotyrosine in proteins. *Methods Enzymol* 99:387-402.

Ficarro S B, McCleland M L, Stukenberg P T, Burke D J, Ross M M, Shabanowitz J, Hunt D F & White F M (2002) Phosphoproteome analysis by mass spectrometry and its application to *Saccharomyces cerevisiae*. *Nature Biotechnol* 20:301-305.

Fischer E H (1997) Cellular regulation by protein phosphorylation: a historical overview. *Biofactors* 6:367-374.

Gaberc-Porekar V & Menart V (2001) Perspectives of immobilized-metal affinity chromatography. *J Biochem Biophys Methods* 49:335-360.

Hochuli E (1988) Large-scale chromatography of recombinant proteins. *J Chromatogr* 444:293-302.

Hochuli E, Dobeli H & Schacher A (1987) New metal chelate adsorbent selective for proteins and peptides containing neighbouring histidine residues. *J Chromatogr* 411:177-184.

Hunter T (1995) Protein kinases and phosphatases: the yin and yang of protein phosphorylation and signaling. *Cell* 80:225-236.

Hunter T (1998) The Croonian Lecture 1997: The phosphorylation of proteins on tyrosine: its role in cell growth and disease. *Philos Trans R Soc Lond B Biol Sci* 353:583-605.

Hunter T (2000) Signaling—2000 and beyond. *Cell* 100:113-127.

Johnson A R & Dekker E E (1996) Woodward's reagent K inactivation of *Escherichia coli* L-threonine dehydrogenase: increased absorbance at 340-350 nm is due to modification of cysteine and histidine residues, not aspartate or glutamate carboxyl groups. *Protein Sci* 5:382-390.

Johnson L N & Lewis R J (2001) Structural basis for control by phosphorylation. *Chem Rev* 101:2209-2242.

Kaufmann H, Bailey J E & Fussenegger M (2001) Use of antibodies for detection of phosphorylated proteins separated by two-dimensional gel electrophoresis. *Proteomics* 1:194-199

Lau L F, Schachter J B, Seymour P A & Sanner M A (2002) Tau protein phosphorylation as a therapeutic target in Alzheimer's disease. *Curr Top Med Chem* 2:395-415.

Lee J T, Jr. & McCubrey J A (2002) The Raf/MEK/ERK signal transduction cascade as a target for chemotherapeutic intervention in leukemia. *Leukemia* 16:486-507.

Li S & Dass C (1999) Iron(III)-immobilized metal ion affinity chromatography and mass spectrometry for the purification and characterization of synthetic phosphopeptides. *Anal Biochem* 270:9-14.

Li W & She H (2000) The SH2 and SH3 adapter Nck: a two-gene family and a linker between tyrosine kinases and multiple signaling networks. *Histol Histopathol* 15:947-955.

Mann M, Ong S E, Gronborg M, Steen H, Jensen O N & Pandey A (2002) Analysis of protein phosphorylation using mass spectrometry: deciphering the phosphoproteome. *Trends Biotechnol* 20:261-268.

McCarty J H (1998) The Nck S H2/SH3 adaptor protein: a regulator of multiple intracellular signal transduction events. *Bioessays* 20:913-921.

McMahan S A & Burgess R R (1996) Single-step synthesis and characterization of biotinylated nitrilotriacetic acid, a unique reagent for the detection of histidine-tagged proteins immobilized on nitrocellulose. *Anal Biochem* 236:101-106.

Muszynska G, Andersson L & Porath J (1986) Selective adsorption of phosphoproteins on gel-immobilized ferric chelate. *Biochemistry* 25:6850-6853.

Muszynska G, Dobrowolska G, Medin A, Ekman P & Porath J O (1992) Model studies on iron(III) ion affinity chromatography. II. Interaction of immobilized iron(III) ions with phosphorylated amino acids, peptides and proteins. *J Chromatogr* 604:19-28.

Oda Y, Nagasu T & Chait B T (2001) Enrichment analysis of phosphorylated proteins as a tool for probing the phosphoproteome. *Nature Biotechnol* 19:379-382.

Paoli P, Fiaschi T, Cirri P, Camici G, Manao G, Cappugi G. Raugei G, Moneti G & Ramponi G (1997) Mechanism of acylphosphatase inactivation by Woodward's reagent K. *Biochem J* 328:855-861.

Porath J, Carlsson J, Olsson I & Belfrage G 1975) Metal chelate affinity chromatography, a new approach to protein fractionation. *Nature* 258:598-599.

Porath J & Olin B (1983) Immobilized metal ion affinity adsorption and immobilized metal ion affinity chromatography of biomaterials. Serum protein affinities for gel-immobilized iron and nickel ions. *Biochemistry* 22:1621-1630.

Posewitz M C & Tempst P (1999) Immobilized gallium(III) affinity chromatography of phosphopeptides. *Anal Chem* 71:2883-2892.

Ramadan N & Porath J (1985) Fe3+-hydroxamate as immobilized metal affinity-adsorbent for protein chromatography. *J Chromatogr* 321:93-104.

Raska C S, Parker C E, Dominski Z, Marzluff W F, Glish G L, Pope R M & Borchers C H (2002) Direct MALDI-MS/MS of phosphopeptides affinity-bound to immobilized metal ion affinity chromatography beads. *Anal Chem* 74:3429-3433.

Sawyers C L (2002) Disabling Abl-perspectives on Abl kinase regulation and cancer therapeutics. *Cancer Cell* 1:13-15.

Sefton B M (1991) Measurement of stoichiometry of protein phosphorylation by biosynthetic labeling. *Methods Enzymol* 201:245-251

Sinha U & Brewer J M (1985) A spectrophotometric method for quantitation of carboxyl group modification of proteins using Woodward's Reagent K. *Anal Biochem* 151:327-333.

Smith C M, Radzio-Andzelm E, Madhusudan, Akamine P & Taylor S S (1999) The catalytic subunit of cAMP-dependent protein kinase: prototype for an extended network of communication. *Prog Biophys Mol Biol* 71:313-341.

Steen H, Kuster B & Mann M (2001) Quadrupole time-of-flight versus triple-quadrupole mass spectrometry for the determination of phosphopeptides by precursor ion scanning. *J Mass Spectrom* 36:782-790.

Stensballe A, Andersen S & Jensen ON (2001) Characterization of phosphoproteins from electrophoretic gels by nanoscale Fe(III) affinity chromatography with off-line mass spectrometry analysis. *Proteomics* 1:207-222.

Ukkola 0 & Santaniemi M (2002) Protein tyrosine phosphatase 1B: a new target for the treatment of obesity and associated co-morbidities. *J Intern Med* 251:467-475.

U.S. Pat. No. 4,423,158
U.S. Pat. No. 4,877,830
U.S. Pat. No. 5,047,513

Verri A, Laforenza U, Gastaldi G, Tosco M & Rindi G (2002) Molecular characteristics of small intestinal and renal brush border thiamin transporters in rats. *Biochim Biophys Acta* 1558:187-197.

Xhou W, Merrick B A, Khaledi M G & Tomer K B Detection and sequencing of phosphopeptides affinity bound to immobilized metal ion beads by matrix-assisted laser desorption/ionization mass spectrometry. *J Am Soc Mass Spectrom* 11:273-82.

Yang S J, Jiang S S, Kuo S Y, Hung S H, Tam M F & Pan R L (1999) Localization of a carboxylic residue possibly involved in the inhibition of vacuolar H+-pyrophosphatase by N,N'-dicyclohexylcarbodi-imide. *Biochem J* 342:641-646.

Zhou H, Watts J D & Aebersold R (2001) A systematic approach to the analysis of protein phosphorylation. *Nature Biotechnol* 19:375-378.

It will be understood that various details of the presently claimed subject matter can be changed without departing from the scope of the presently claimed subject matter. Furthermore, the foregoing description is for the purpose of illustration only, and not for the purpose of limitation—the presently claimed subject matter being defined by the claims.

What is claimed is:

1. A composition comprising a membrane having bound carboxy-blocked phosphoprotein, wherein the phosphoprotein is coordinated to a phosphoprotein detection reagent (PPDR) comprising:
   (i) a polydentate chelator coordinated to a metal ion selected from the group consisting of $Fe^{3+}$, $Al^{3+}$, $Yb^{3+}$, and $Ga^{3+}$; and
   (ii) a detectable moiety conjugated to the polydentate chelator at a site other than a potential metal ion coordination site;
   wherein the chelated metal ion selectively binds to a phosphorylated amino acid residue in the phosphoprotein to create a chelator-metal ion-phosphoprotein (CMPP) complex; and the detectable moiety allows the CMPP complex to be detected.

2. The composition of claim 1, wherein the PPDR is soluble in an aqueous medium.

3. The composition of claim 1, wherein the chelator is a tetradentate nitriloacetic acid.

4. The composition of claim 1, wherein the chelator is a tridentate iminodiacetic acid.

5. The composition of claim 1, wherein the metal ion is $Ga^{3+}$.

6. The composition of claim 1, wherein the metal ion is $Fe^{3+}$.

7. The composition of claim 1, wherein the detectable moiety is biotin.

8. The composition of claim 1, further comprising a spacer between the chelator-metal ion moiety and the detectable moiety.

9. A method for preparing a composition comprising a membrane having bound carboxy-blocked phosphoprotein, wherein the phosphoprotein is coordinated to a phosphoprotein detection reagent (PPDR), the method comprising:
   (a) reacting a polydentate chelator donor molecule with a detectable moiety donor under conditions wherein a detectable moiety is transferred to a polydentate chelator at a site other than a coordination site to form a chelator-detectable moiety complex;
   (b) chelating a metal ion selected from the group consisting of $Fe^{3+}$, $Al^{3+}$, $Yb^{3+}$, and $Ga^{3+}$ to the polydentate chelator to form a PPDR, wherein the PPDR is soluble in aqueous medium; and
   (c) contacting a membrane having bound carboxy-blocked phosphoprotein with the PPDR.

10. The method of claim 9, wherein the chelator donor molecule is selected from the group consisting of 2-(aminooxyethyl)iminodiacetic acid (AIDA), aminobutyl-nitriloacetic acid (AB-NTA), and iminodiacetic acid (IDA).

11. The method of claim 9, wherein the detectable moiety donor is selected from the group consisting of sulfo-N-hydroxysuccinimidyl-biotin (sulfo-NHS-biotin), sulfosuccinimidyl-6-(biotinamido) hexanoate (sulfo-NHS-LC-biotin), sulfosuccinimidyl-6-(biotinamido)-6-hexanimido hexanoate (sulfo-NHS-LC-LC-biotin), and penta-fluorophenyl-biotin.

12. The method of claim 9, wherein the detectable moiety donor is present in the reacting step in a molar excess over the polydentate chelator donor molecule.

13. The method of claim 9, wherein the chelator-detectable moiety complex and a metal ion-containing solution are present in equimolar concentrations in the chelating step.

14. A kit comprising:
   (a) a phosphoprotein detection reagent (PPDR) comprising:
      (i) a polydentate chelator coordinated to a metal ion selected from the group consisting of $Fe^{3+}$, $Al^{3+}$, $Yb^{3+}$, and $Ga^{3+}$; and
      (ii) a detectable moiety conjugated to the polydentate chelator at a site other than a potential metal ion coordination site,
      wherein the chelated metal ion selectively binds to a phosphorylated amino acid residue in a phosphoprotein if present to create a chelator-metal ion-phosphoprotein (CMPP) complex, and the detectable moiety allows the CMPP complex to be detected if present;
   (b) a membrane;
   (c) a carboxy-blocking reagent, and
   (d) instructions for using the PPDR.

15. The kit of claim 14, further comprising a secondary reagent for detecting the PPDR.

16. The kit of claim 14, wherein the phosphoprotein detection reagent (PPDR) is soluble in aqueous medium.

17. A composition comprising a membrane having bound carboxy-blocked phosphoprotein, wherein the phosphoprotein is coordinated to a phosphoprotein detection reagent (PPDR) comprising a chelator and a detectable moiety conjugated to the chelator in a binding solution with a pH ranging from about 5.0 to about 7.0, wherein:
   (i) the chelator comprises a tetradentate nitriloacetic acid or a tridentate iminodiacetic acid coordinated to a metal ion selected from the group consisting of $Fe^{3+}$, $Al^{3+}$, $Yb^{3+}$, and $Ga^{3+}$;
   (ii) the chelated metal ion selectively binds to a phosphorylated amino acid residue in the phosphoprotein to create a chelator-metal ion-phosphoprotein CMPP) complex, and the detectable moiety allows the CMPP complex to be detected; and
   (iii) the PPDR is soluble in aqueous medium.

18. The composition of claim 17, wherein the metal ion is $Ga^{3+}$.

19. The composition of claim 17, wherein the metal ion is $Fe^{3+}$.

20. The composition of claim 17, wherein the detectable moiety is biotin.

21. The composition of claim 17, further comprising a spacer between the chelator and the detectable moiety.

22. A composition comprising:
   (a) a membrane;
   (b) a carboxy-blocked phosphoprotein bound to the membrane;
   (c) a metal ion selected from the group consisting of $Fe^{3+}$, $Al^{3+}$, $Yb^{3+}$, and $Ga^{3+}$;
   (d) a phosphoprotein detection reagent (PPDR) comprising a chelator and a detectable moiety, wherein:
      (i) the detectable moiety is conjugated to the chelator at a site other than a potential metal ion coordination site;
      (ii) the chelator comprises a polydentate chelator coordinated to the metal ion to form a chelator-metal ion moiety;
      (iii) the chelator-metal ion moiety selectively binds to a phosphorylated amino acid residue in the phosphoprotein to create a chelator-metal ion-phosphoprotein (CMPP) complex; and
      (iv) the detectable moiety allows the CMPP complex to be detected; and
   (e) a binding solution having a pH ranging from about 5.0 to about 7.0, wherein the chelated metal ion selectively binds to the phosphorylated amino acid reside in the phosphoprotein in the binding solution.

23. The kit of claim 14, wherein the kit further comprises a binding solution having a pH ranging from about 5.0 to about 7.0.

24. The composition of claim 1, comprising a binding solution with a pH ranging from about 5.0 to about 7.0.

25. The method of claim 9, wherein the membrane having bound carboxy-blocked phosphoprotein is prepared by contacting a membrane having bound phosphoprotein with one of the groups consisting of methanolic HCl, a carbodiimide, and Woodward's Reagent "K".

* * * * *